(12) United States Patent
Lee et al.

(10) Patent No.: US 6,403,792 B1
(45) Date of Patent: Jun. 11, 2002

(54) SULFONYL ISATIN COMPOUNDS AND METHODS OF BLOCKING APOPTOSIS THEREWITH

(75) Inventors: Dennis Lee, Swarthmore, PA (US); Scott Allen Long, Valley Park, MO (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/445,616

(22) PCT Filed: Jul. 30, 1998

(86) PCT No.: PCT/US98/15935

§ 371 (c)(1),
(2), (4) Date: Dec. 9, 1999

(87) PCT Pub. No.: WO99/06367

PCT Pub. Date: Feb. 11, 1999

Related U.S. Application Data

(60) Provisional application No. 60/054,255, filed on Jul. 30, 1997.

(51) Int. Cl.[7] .................... C07D 403/08; C07D 413/00; C07D 401/08; C07D 209/10

(52) U.S. Cl. ...................... 544/144; 544/373; 546/198; 548/467; 548/485

(58) Field of Search ................ 548/467, 485; 546/198; 544/144, 373; 514/252.15, 320, 299

(56) References Cited

U.S. PATENT DOCUMENTS

| | | | |
|---|---|---|---|
| 4,395,559 A | 7/1983 | Fothergill et al. | 548/485 |
| 4,556,673 A | 12/1985 | Andersen et al. | 514/414 |
| 5,728,712 A | 3/1998 | Montana et al. | 514/369 |

OTHER PUBLICATIONS

Springer et al., "Activation of the caspase–3 apoptotic cascade in traumatic spinal cord injury", *Nature Medicine* 5(8), pp. 943–946 (1999).

*Primary Examiner*—Floyd D. Higel
*Assistant Examiner*—Ebenezer Sackey
(74) *Attorney, Agent, or Firm*—Loretta J. Henderson; Dara L. Dinner; William T. King

(57) ABSTRACT

The present invention is to novel sulfonyl isatin compounds of Formula (I), their pharmaceutical compositions, and the novel inhibition of caspases for use in the treatment of apoptosis, and disease states caused by excessive or inappropriate cell death.

17 Claims, No Drawings

SULFONYL ISATIN COMPOUNDS AND METHODS OF BLOCKING APOPTOSIS THEREWITH

This application is a 371 of PCT/US98/15935 filed Jul. 30, 1998 which claims benefit of 60/054,255 filed Jul. 30, 1997.

FIELD OF THE INVENTION

The present invention is to the discovery of a new method to block excessive or inappropriate apoptosis in a mammal.

BACKGROUND

It has been recognized for over a century that there are different forms of cell death. One form of cell death, necrosis, is usually the result of severe trauma and is a process that involves loss of membrane integrity and uncontrolled release of cellular contents, often giving rise to inflammatory responses. In contrast, apoptosis is a more physiological process that occurs in a controlled manner and is generally non-inflammatory in nature. For this reason apoptosis is often referred to as programmed cell death. The name itself (apoptosis: Greek for "dropping off", for example leaves from trees) implies a cell death that is part of a normal physiological process (Kerr et al., Br. J. Cancer, 26: 239–257 (1972)).

Apoptosis appears to be a carefully controlled series of cellular events which ultimately leads to death of the cell. This process for elimination of unwanted cells is active and requires expenditure of cellular energy. The morphological characteristics of apoptosis include cell shrinkage and loss of cell-cell contact, condensation of nuclear chromatin followed by fragmentation, the appearance of membrane ruffling, membrane blebbing and apoptotic bodies. At the end of the process, neighboring cells and macrophages phagocytose the fragments from the apoptotic cell. The process can be very fast, occurring in as little as a few hours (Bright et al., Biosci. Rep., 14: 67–82 (1994)).

The best defined biochemical event of apoptosis involves the orderly destruction of nuclear DNA. Signals for apoptosis promote the activation of specific calcium- and magnesium-dependent endonucleoases that cleave the double stranded DNA at linker regions between nucleosomes. This results in production of DNA fragments that are multiples of 180–200 base pair fragments (Bergamaschi et al., Haematologica, 79: 86–93 (1994); Stewart, JNCI, 86: 1286–1296 (1994)). When examined by agarose gel electrophoresis, these multiple fragments form a ladder pattern that is characteristic for most cells undergoing apoptosis.

There are numerous stimuli that can signal cells to initiate or promote cellular apoptosis, and these can be different in different cells. These stimuli can include glucocorticoids, TNFa, growth factor deprivation, some viral proteins, radiation and anticancer drugs. Some of these stimuli can induce their signals through a variety of cell surface receptors, such as the TNF/nerve growth factor family of receptors, which include CD40 and Fas/Apo-1 (Bright et al., supra). Given this diversity in stimuli that cause apoptosis it has been difficult to map out the signal transduction pathways and molecular factors involved in apoptosis. However, there is evidence for specific molecules being involved in apoptosis.

The best evidence for specific molecules that are essential for apoptosis comes from the study of the nematode C. elegans. In this system, genes that appear to be required for induction of apoptosis are Ced-3 and Ced-4. These genes must function in the dying cells and, if either gene is inactivated by mutation, cell death fails to occur (Yuan et al., Devel. Biol., 138: 33–41 (1990)). In mammals, genes that have been linked with induction of apoptosis include the proto-oncogene c-myc and the tumor suppresser gene p53 (Bright et al., supra: Symonds et al., Cell, 78: 703–711 (1994)).

In this critical determination of whether or not to undergo apoptosis, it is not surprising that these are genes that program for proteins that inhibit apoptosis. An example in C. elegans is Ced-9. When it is abnormally activated, cells survive that would normally die and, conversely, when Ced-9 is inactivated cells die that would normally live (Stewart, B. W., supra). A mammalian counterpart is bcl-2, which had been identified as a cancer-causing oncogene. This gene inhibits apoptosis when its product is overexpressed in a variety of mammalian cells, rendering them less sensitive to radiation, cytotoxic drugs and apoptotic signals such as c-myc (Bright et al., supra). Some virus protein have taken advantage of this ability of specific proteins to block apoptosis by producing homologous viral proteins with analogous functions. An example of such a situation is a protein produced by the Epstein Barr virus that is similar to bcl-2, which prevents cell death and thus enhances viral production (Wells et al., J. Reprod. Fertil., 101: 385–391 (1994)). In contrast, some proteins may bind to and inhibit the function of bcl-2 protein, an example being the protein bax (Stewart, B. W., supra). The overall picture that has developed is that entry into apoptosis is regulated by a careful balancing act between specific gene products that promote or inhibit apoptosis (Barinaga, Science, 263: 754–756 (1994).

Apoptosis is an important part of normal physiology. The two most often sited examples of this are fetal development and immune cell development. In development of the fetal nervous system, over half of the neurons that exist in the early fetus are lost by apoptosis during development to form the mature brain (Bergamaschi et al., Haematologica, 79: 86–93 (1994)). In the production of immune competent T cells (and to a lesser extent evidence exists for B cells), a selection process occurs that eliminates cells that recognize and react against self. This selection process is thought to occur in an apoptotic manner within areas of immune cell maturation (Williams, G. T., J. Pathol., 173: 1–4 (1994); Krammer et al., Curr. Opin. Immunol., 6: 279–289 (1994)).

Dysregulation of apoptosis can play an important role in disease states, and diseases can be caused by both excessive or too little apoptosis occurring. An example of diseases associated with too little apoptosis would be certain cancers. There is a follicular B-cell lymphoma associated with an aberrant expression of functional bcl-2 and an inhibition of apoptosis in that cell (Bergamaschi et al., supra). There are numerous reports that associate deletion or mutation of p53 with the inhibition of apoptosis and the production of cancerous cells (Kerr et al., Cancer, 73: 2013–2026 (1994); Ashwell et al., Immunol. Today, 15: 147–151 (1994)). In contrast, one example of excessive or inappropriate apoptosis is the loss of neuronal cells that occurs in Alzheimer disease, possible induced by b-amyloid peptides (Barr et al., BioTechnology, 12: 487–493 (1994)). Other examples include excessive apoptosis of $CD4^+$ T cells that occurs in HIV infection, of cardiac myocytes during infarction/reperfusion and of neuronal cells during ischemia (Bergamaschi et al., supra); Barr et al., supra).

Some pharmacological agents attempt to counteract the lack of apoptosis that is observed in cancers. Examples includes topoisomerase II inhibitors, such as the epipodophyllotoxins, and antimetabolites, such as ara-c, which have been reported to enhance apoptosis in cancer cells (Ashwell et al., supra). In many cases with these anti-cancer drugs, the exact mechanism for the induction of apoptosis remains to be elucidated.

In the last few years, evidence has built that ICE and proteins homologous to ICE (Caspases) play a key role in apoptosis. This area of research has been spurred by the observation of homology between the protein coded by Ced-3, a gene known to be critical for C. Elegans apoptosis, and ICE (Caspase 1). These two proteins share 29% amino acid identity, and complete identity in the 5 amino acid portion thought to be responsible for protease activity (QACRG) (Yuan et al., Cell, 75: 641–652 (1993)). Additional homologies are observed between ICE and the product of the nedd-2 gene in mice, a gene suspected of involvement in apoptosis in the developing brain (Kumar et al., Genes Dev., 8: 1613–1626 (1994)) and Ich-1 (Caspase 2) and CPP32 (Caspase 3), human counterparts of nedd-2 isolated from human brain cDNA libraries (Wang et al., Cell, 78: 739–750 (1994); Fernandes-Alnemiri et al., J. Biol. Chem., 269: 30761–30764 (1994)).

Further proof for the role of these proteins in apoptosis comes from transfection studies. Over expression of murine ICE caused fibroblasts to undergo programmed cell death in a transient transfection assay (Miura et al., Cell, 75: 653–660 (1993)). Cell death could be prevented by point mutations in the transfected gene in the region of greatest homology between ICE and Ced-3. As very strong support for the role of ICE in apoptosis, the authors showed that ICE transfection-induced apoptosis could be antagonized by overexpression of bcl-2, the mammalian oncogene that can prevent programmed cell death (Miura et al., supra). Additional experiments were performed using the crmA gene. This gene of the cowpox virus encodes a serpin protein, a family of proteins that are inhibitors of proteases (Ray et al., Cell, 69: 597–604 (1992)). Specifically, the protein of crmA has been shown to inhibit processing of pro-interleukin-lb by ICE, (Gagliardini et al. Science, 263: 826–828 (1994)) showed that microinjection of the crmA gene into dorsal root ganglion neurons prevented cell death induced by nerve growth factor deprivation. This result shows that ICE is involved in neuronal cell apoptosis. A more direct demonstration of ICE involvement comes from experiments in which ICE transfection is coupled with the co-expression of crmA, demonstrating a crmA-induced suppression of the ICE-induced apoptosis response (Miura et al., supra: Wang et al., supra).

In addition to ICE, researchers have examined the ability of Caspase genes to promote apoptosis. (Kumar et al. supra) demonstrated that over expression of nedd-2 in fibroblasts and neuroblastoma cells resulted in cell death by apoptosis and that this apoptosis could also be suppressed by expression of the bcl-2 gene. Most recently, Wang et al., (Wang et al., supra) examined the over expression of Ich-1 in a number of mammalian cells. Expression resulted in cell apoptosis, which could be antagonized by bcl-2 co-expression. Mutation of a cysteine residue, contained within the QACRG motif and presumed to be critical for protease function, to serine abolished apoptotic activity.

Further evidence for a role of a cysteine protease in apoptosis comes from a recent report by Lazebnik et al. (Nature, 371: 346–347 (1994)). These authors have used a cell-free system to mimic and study apoptosis. In their system there is a protease activity that cleaves the enzyme poly(ADP-ribose) polymerase at a site identical to a cleavage site in pre-interleukin-lb. However, this yet to be isolated protease and ICE appear to be different and to act on different substrate proteins. Blockade of protease activity in the system, using non-selective cysteine protease inhibitors, resulted in inhibition of apoptosis.

Taken together, the above evidence provides striking involvement of Caspases in the induction of apoptosis in mammalian cells. Brain interluekin-1 has been reported to be elevated in Alzheimer disease and Down syndrome (Griffin et al., Proc. Natl. Acad. Sci. U.S.A., 86: 7611–7615 (1989)). There are also reports that interluekin-1 can increase the mRNA and production of b-amyloid protein, a major component of senile plaques in Alzheimer disease as well as in brains of people with Down syndrome and with aging (Forloni et al., Mol. Brain Res., 16: 128–134 (1992); Buxbaum et al., Proc. Natl. Acad. Sci. U.S.A., 89: 10075–10078 (1992); Goldgaber et al., Proc. Natl. Acad. Sci. U.S.A., 86: 7606–7610 (1989)). These reports can be viewed as additional evidence for the involvement of ICE in these diseases and the need for use of a novel therapeutic agent and therapy thereby.

To date, no useful therapeutic strategies have blocked excessive or inappropriate apoptosis. In one patent application, EPO 0 533 226 a novel peptide structure is disclosed which is said to be useful for determining the activity of ICE, and therefore useful in the diagnoses and monitoring of IL-1 mediated diseases. Therefore, a need exists to find better therapeutic agents which have non-toxic pharmacological and toxicological profiles for use in mammals. These compounds should block excessive or inappropriate apoptosis cells, and hence provide treatment for diseases and conditions in which this condition appears.

SUMMARY OF THE INVENTION

The present invention is to the novel compounds of Formula (I), their pharmaceutical compositions, and to the novel inhibition of caspases for use in the treatment of apoptosis, and disease states caused by excessive or inappropriate cell death. The compounds of Formula I are most effective in inhibiting caspases 3 and 7.

Another aspect of the present invention is to a pharmaceutical composition comprising a compound of Formula (I), or a pharmaceutically acceptable salt thereof, and a pharmaceutically acceptable carrier or diluent.

Another aspect of the present invention is to a method for the treatment of diseases or disorders associated with excessive IL-lb convertase activity, in a mammal in need thereof, which method comprises administering to said mammal an effective amount of a compound of Formula (I), or a pharmaceutically acceptable salt thereof.

Another aspect of the present invention is to a method of preventing or reducing apoptosis in a mammal, preferably a human, in need of such treatment which method comprises administering to said mammal or human an effective amount of a compound of Formula (I), or a pharmaceutically acceptable salt thereof.

Another aspect of the present invention is to a method of blocking or decreasing the production of IL-lb and/or TNF, in a mammal, preferably a human, in need of such treatment which method comprises administering to said mammal or human an effective amount of a compound of Formula (I), or a pharmaceutically acceptable salt thereof.

The compounds of Formula I are represented by the structure

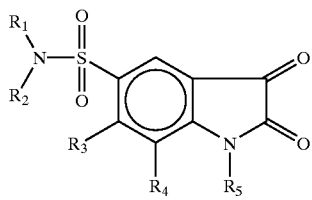

(I)

wherein
R₁ is hydrogen, or $C_{1-4}$ alkyl;
R₂ is $C_{1-10}$ alkyl, optionally substituted aryl$C_{1-4}$alkyl, optionally substituted heteroaryl $C_{1-4}$ alkyl, optionally substituted $C_{3-7}$ cycloalkyl, or R₁ and R₂ together with the nitrogen to which they are attached from a 3 to 10 membered ring which optionally contains an additional heteroatom selected from oxygen, nitrogen or sulfur;
R₃ and R₄ are $C_{1-6}$alkyl, hydrogen, nitro or halogen and R₅ is $C_{1-6}$alkyl, hydrogen, arylalkyl or heteroarylalkyl.

Preferably R₁ and R₂ are joined for form a five membered nitrogen containing ring. It is recognized that the alkyl group in the arylalkyl or heteroalkyl moiety may be branched or straight, such as a methylene or a substituted methylene group, i.e., —CH(CH₃)—aryl. The optionally substituted aryl moiety of the arylalkyl group, may be substituted one to three times independently by hydroxy, halogen, alkyl or alkoxy. R₅ is preferably benzyl.

Compounds exemplified by Formula (I) include, but are not limited to:
(S)-(+)-5-[1-(2-Methoxymethylpyrrolidinyl)sulfonyl]isatin
DL-5-[1-(2-(Hydroxyethyl)piperidinyl)sulfonyl]isatin
(+/−)-5-[1-(3-Hydroxymethyl)piperidinyl)sulfonyl]isatin
(S)-(+)-5-[1-(2-Hydroxymethylpyrrolidinyl)sulfonyl]isatin
(S)-(+)-5-[1-(2-Benzyloxycarbonylpyrrolidinyl)sulfonyl]isatin
5-[N-(N-Methyl-2-hydroxyethylamino)sulfonyl]isatin
5-[N-(N-Methyl-2-(4-pyridine)ethylamino)sulfonyl]isatin
5-[N-(N'-Benzylpiperazine)sulfonyl]isatin
(R)-(−)-5-[1-(2-Methoxymethylpyrrolidinyl)sulfonyl]isatin
(S)-(+)-5-[1-(2-Methoxycarbonylpyrrolidinyl)sulfonyl]isatin
5-[N-(N-Methylanilino)sulfonyl]isatin
(S)-(+)-5-[1-(2-t-Butoxycarbonylpyrrolidinyl)sulfonyl]isatin
(S)-(+)-5-[1-(2-N,N-Dimethylaminocarbonylpyrrolidinyl)sulfonyl]isatin
(S)-(+)-5-[1-(2-Carboxypyrrolidinyl)sulfonyl]isatin
(S)-(+)-1-Isopropyl-5-[1-(2-Methoxymethylpyrrolidinyl)sulfonyl]isatin
5-[N-(N-Methyl-2-cyanoethylamino)sulfonyl]isatin
(S)-(+)-5-[1-(2-(Anilinomethyl)pyrrolidinyl)sulfonyl]isatin
5-[N-(Ethoxycarbonylmethylamino)sulfonyl]isatin
(+/−)-5-[1-(3-(N-Methyl-N-Boc-amino)pyrrolidinyl)sulfonyl]isatin
(+/−)-5-[1-(3-(N-Methyl-N-phenethylcarbonylamino)pyrrolidinyl)sulfonyl]isatin
(+/−)-5-[1-(3-(N-Methylamino)pyrrolidinyl)sulfonyl]isatin trifluoro acetic acid salt
5-[N-(N-methyl-2-Methoxyethylamino)sulfonyl]isatin
(S)-(+)-5-[1-(2-Phenoxymethylpyrrolidinyl)sulfonyl]isatin
(S)-(+)-5-[1-(2-Thiophenoxymethylpyrrolidinyl)sulfonyl]isatin
(S)-(+)-5-[1-(2-Phenylaminocarbonylpyrrolidinyl)sulfonyl]isatin
(+/−)-5-[1-(3-Chloromethylpiperidinyl)sulfonyl]isatin
5-[1-(4-Hydroxypiperidinyl)sulfonyl]isatin
5-[N-(Morpholino)sulfonyl]isatin
5-[N-(N-Methyl-2-phenethylamino)sulfonyl]isatin
(S)-(+)-1-Benzyl-5-[1-(2-thiophenoxymethylpyrrolidinyl)sulfonyl]isatin
(+/−)-5-[1-(3-(N-methylbenzamide)pyrrolidinyl)sulfonyl]isatin
5-[1-(2-(Phenylsulfinylmethyl)pyrrolidinyl)sulfonyl]isatin
5-[1-(azetidinyl)sulfonyl]isatin
(S)-(+)-5-[1-(2-(4-Methylphenoxymethyl)pyrrolidinyl)sulfonyl]isatin
(S)-(+)-5-[1-(2-(4-Methoxyphenoxymethyl)pyrrolidinyl)sulfonyl]isatin
(S)-(+)-5-[1-(2-(4-Chlorophenoxymethyl)pyrrolidinyl)sulfonyl]isatin
(S)-(+)-5-[1-(2-(3,4-Dichlorophenoxymethyl)pyrrolidinyl)sulfonyl]isatin
5-[1-(2-(4-chlorophenoxy)azetidinyl)sulfonyl]isatin
5-[1-(Homopiperidinyl)sulfonyl]isatin
(S)-(+)-1-(3-Chlorobenzyl)-5-[1-(2-phenoxymethylpyrrolidinyl)sulfonyl]isatin
(S)-(+)-1-Benzyl-5-[1-(2-phenoxymethylpyrrolidinyl)sulfonyl]isatin
5-[1-(Pyrrolidinyl)sulfonyl]isatin
(S)-(+)-1-(4-Methylbenzyl)-5-[1-(2-phenoxymethylpyrrolidinyl)sulfonyl]isatin
(S)-(+)-1-(4-Chlorobenzyl)-5-[1-(2-phenoxymethylpyrrolidinyl)sulfonyl]isatin
(S)-(+)-1-(3,4-Dichlorobenzyl)-5-[1-(2-phenoxymethylpyrrolidinyl)sulfonyl]isatin
(S)-(+)-1-(2-Methylnapthalene)-5-[1-(2-phenoxymethylpyrrolidinyl)sulfonyl]isatin
(S)-(+)-1-[4-(1,2,3-Thiadiazole)benzyl]-5-[1-(2-phenoxymethylpyrrolidinyl)sulfonyl]isatin
(S)-(+)-1-Allyl-5-[1-(2-phenoxymethylpyrrolidinyl)sulfonyl]isatin
(S)-(+)-1-(2-Phenylethyl)-5-[1-(2-phenoxymethylpyrrolidinyl)sulfonyl]isatin
(S)-(+)-1-(3-Phenylpropyl)-5-[1-(2-phenoxymethylpyrrolidinyl)sulfonyl]isatin
(S)-(+)-1-(4-Methoxybenzyl)-5-[1-(2-phenoxymethylpyrrolidinyl)sulfonyl]isatin
(S)-(+)-1-Cyclohexylmethyl-5-[1-(2-phenoxymethylpyrrolidinyl)sulfonyl]isatin
(S)-(+)-1-Methyl-5-[1-(2-phenoxymethylpyrrolidinyl)sulfonyl]isatin
(S)-(+)-1-(3-Iodobenzyl)-5-[1-(2-phenoxymethylpyrrolidinyl)sulfonyl]isatin
(S)-(+)-1-Methyl-5-[1-(2-(N-methylanilinomethyl)pyrrolidinyl)sulfonyl]isatin
(S)-(+)-1-(t-Butoxycarbonylmethyl)-5-[1-(2-phenoxymethylpyrrolidinyl)sulfonyl]isatin
(S)-(+)-1-(Acetic acid)-5-[1-(2-phenoxymethylpyrrolidinyl)sulfonyl]isatin
(S)-(+)-1-Methyl-5-[1-(2-(anilinomethyl)pyrrolidinyl)sulfonyl]isatin
(R)-(−)-5-[1-(2-(anilinomethyl)pyrrolidinyl)sulfonyl]isatin
(S)-(+)-1-Benzyl-5-[1-(2-(anilinomethyl)pyrrolidinyl)sulfonyl]isatin
(S)-(+)-1-Cyanomethyl-5-[1-(2-phenoxymethylpyrrolidinyl)sulfonyl]isatin
(S)-(+)-1-[2-(2-Ethyl)-1-methylpyrrolidine]-5-[1-(2-phenoxymethylpyrrolidinyl)sulfonyl]isatin
(S)-(+)-1-(3-Methylsulfonylbenzyl)-5-[1-(2-phenoxymethylpyrrolidinyl)sulfonyl]isatin
(S)-(+)-1-(3-Carboxamidobenzyl)-5-[1-(2-phenoxymethylpyrrolidinyl)sulfonyl]isatin (R)-5-[1-(2-Phenethylpyrrolidinyl)sulfonyl]isatin
5-[1-(2-Phenoxymethylpiperidinyl)sulfonyl]isatin
(S)-5-[1-(1-Methoxy-2-phenethylpyrrolidinyl)sulfonyl]isatin
(S)-1-(4-Pyridinylmethyl)-5-[1-(2-phenoxymethylpyrrolidinyl)sulfonyl]isatin
(S)-1-(3-Pyridinylmethyl)-5-[1-(2-phenoxymethylpyrrolidinyl)sulfonyl]isatin
5-[1-(N-Acetylhomopiperazine)sulfonyl]isatin
5-[1-(Thiazolidine)sulfonyl]isatin
5-[1-(4-Piperanoylpiperazine)sulfonyl]isatin
(S)-1-[3-(t-Butoxycarbonyl)benzyl]-5-[1-(2-phenoxymethylpyrrolidinyl)sulfonyl]isatin
(S)-1-(3-Carboxyphenylmethyl)-5-[1-(2-phenoxymethylpyrrolidinyl)sulfonyl]isatin
5-[1-(4-Acetyl-(2-thiophene)-homopiperazine)sulfonyl]isatin
(S)-1-(4-Cyanophenylmethyl)-5-[1-(2-phenoxymethylpyrrolidinyl)sulfonyl]isatin
(S)-1-(3,4-Methylenedioxybenzyl)-5-[1-(2-phenoxymethylpyrrolidinyl)sulfonyl]isatin
(S)-1-(Methoxymethyl)-5-[1-(2-phenoxymethylpyrrolidinyl)sulfonyl]isatin
(S)-1-[3-(t-Butoxycarbonyl)propyl]-5-[1-(2-phenoxymethylpyrrolidinyl)sulfonyl]isatin
(S)-1-(3-Carboxypropyl)-5-[1-(2-phenoxymethylpyrrolidinyl)sulfonyl]isatin
(S)-1-[4-(t-Butoxycarbonyl)phenylmethyl]-5-[1-(2-phenoxymethylpyrrolidinyl)sulfonyl]isatin
(S)-1-(4-Carboxyphenylmethyl)-5-[1-(2-phenoxymethylpyrrolidinyl)sulfonyl]isatin The term "excessive IL-lb convertase activity" is used herein to mean an excessive expression of the protein, or activation of the enzyme.

The term "$C_{1-6}$ alkyl" or "alkyl" is used herein to mean both straight and branched chain radicals of 1 to 6 carbon atoms, unless the chain length is otherwise specified, including, but not limited to, methyl, ethyl, n-propyl, iso-propyl, n-butyl, sec-butyl, iso-butyl, tert-butyl, and the like.

The term "heteroaryl" (on its own or in any combination, such as "heteroaryloxy", or "heteroaryl alkyl") is used herein to mean a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, oxadiazole, tetrazole, thiazole, thiadiazole, triazole, imidazole, benzimidazole, benzothiaphene, benzopyrrole, or benzofuran.

The term "aryl" (on its own or in any combination, such as "aryloxy", or "arylalkyl") is used herein to mean a phenyl and naphthyl ring.

The term "cycloalkyl" is used herein to mean cyclic radicals, preferably of 3 to 7 carbons, including but not limited to cyclopropyl, cyclopentyl, cyclohexyl, and the like.

The term "halo" or "halogens", is used herein to include, unless otherwise specified, chloro, fluoro, bromo and iodo.

The present invention contains the inhibition of caspases by compounds of Formula (I). What is meant by the term "caspases" are fragment, homologs, analogs and derivatives of the polypeptides Interleukin-lb converting enzyme (or convertase). These analogs are structurally related to the caspase family. They generally encode a protein(s) which exhibits high homology to the human ICE over the entire sequence. Preferably, the pentapeptide QACRG is conserved. The caspases, which may include many natural allelic variants (such as substitutions, deletion or addition of nucleotides) does not substantially alter the function of the encoded polypeptide. That is they retain essentially the same biological function or activity as the ICE protease, although it is recognized that the biological function may be enhanced or reduced activity. The suitable activity is not IL-lb convertase activity, but the ability to induce apoptosis or involved in programmed cell death in some manner. Suitable caspases encompasses within this invention are those described in PCT US94/07127 filed Jun. 23, 1994; and in U.S. Ser. No. 08/334,251, filed Nov. 1, 1994, whose disclosures are incorporated herein by reference in their entirety.

The term "blocking or inhibiting, or decreasing the production of IL-lb and/or TNF" as used herein refers to:

a) a decrease of excessive levels, or a down regulation, of the cytokine in a human to normal or sub-normal levels by inhibition of the in vivo release of the cytokine; or b) a down regulation, at the genomic level, of excessive in vivo levels of the cytokine (IL-1 or TNF) in a human to normal or sub-normal levels; or c) a down regulation, by inhibition of the direct synthesis of the cytokine (IL-1, or TNF) as a postranslational event; or d) a down regulation, at the translational level, of excessive in vivo levels of the cytokine (IL-1, or TNF) in a human to normal or sub-normal levels.

The blocking or inhibiting, or decreasing the production of IL-lb and/or TNF is a discovery that the compounds of Formula (I) are inhibitors of the cytokines, IL-1 and TNF is based upon the effects of the compounds of Formulas (I) on the production of the IL-1 and TNF in in vitro and in vivo assays which are well known and recognized in the art, some of which are described herein.

Compound of the present invention may be synthesized in accordance with the schemes illustrated below.

5-Alkylaminosulfonylisatins

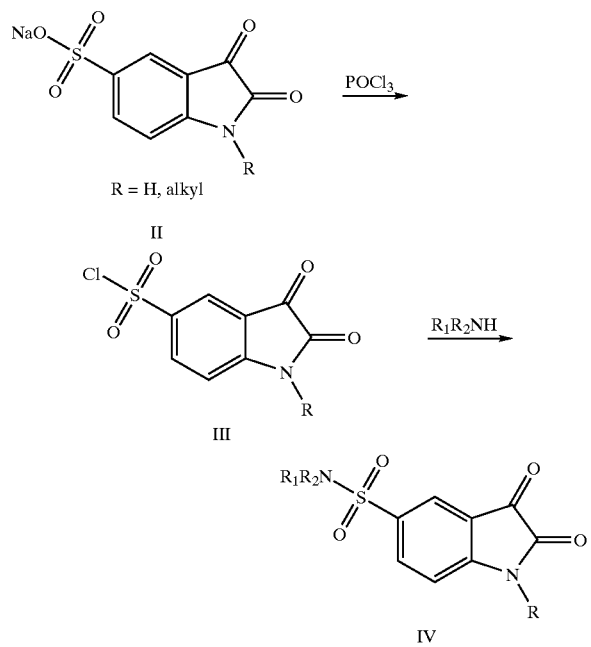

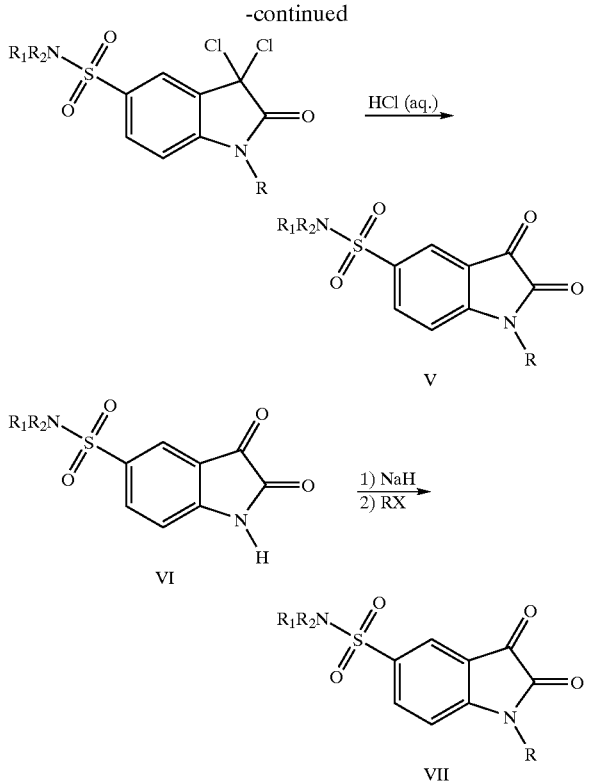

N-Alkylisatin derivatives are prepared either by direct alkylation of isatin or via syntheses of the isatin ring using one of the procedures described by Popp, F. D., *Advances in Heterocyclic Chemistry*, 1975, 18, 1–58. 1-Alkyl-5-isatinsulfonic acids (R=H, alkyl) are prepared according to the procedure as described by Stunzi, H., *Aust. J. Chem.*, 1981, 34, 365. 5-Isatinsulfonic acid, sodium salt or their N-alkyl derivatives can be treated with phosphorus oxychloride in organic solvents such as sulfalane at temperatures ranging from 50–80° C. in order to obtain the corresponding 5-chlorosulfonylisatins (Martinez, F; Naarmann; H. *Synth. Met.*, 1990, 39, 195), the direct precursors to the novel compounds of this invention. Treatment of the chlorosulfonyl derivative with a secondary amine in organic solvents such as tetrahydrofuran, methylene chloride or dimethylformamide with or without the addition of a tertiary amine base such as triethylamine yields the 5-alkylaminosulfonylisatin or its N-alkyl derivative. Alternatively, treatment of the alkylaminosulfonyl-3,3-dichloro-2-oxindole derivative with an aqueous acid such as HCl with or without the presence of a cosolvent such as tetrahydrofuran, dimethylformamide, or methanol also yields the 5-alkylaminosulfonylisatin. The 5-alkylaminosulfonylisatin derivative may be alkylated (Tacconi, Von G; Righetti, P. P.; Desimoni, G.; *J. Prakt. Chem.*, 1973, 315, 339) by deprotonation by a base such as sodium hydride in organic solvents such as dimethylformamide and treatment of the resulting salt with an alkyl halide at temperatures ranging from 25–80° C. to give 1-alkyl-5-alkylaminosulfonylisatin.

EXAMPLE 1

(S)-(+)-5-[1-(2-Methoxymethylpyrrolidinyl) sulfonyl]isatin 1a) 5-Chlorosulfonylisatin To a mixture of isatinsulfonic acid, sodium salt dihydrate (10 g, 35.1 mmol) and 50 mL tetramethylene sulfone was added phosphorus oxychloride (16.5 mL, 177 mmol). The resulting mixture was heated at 60° C. for 3 hours. Cool the mixture to 0° C. and cautiously add 120 mL of water. Filter the resulting green solid and wash with water. Dissolve the solid in 100 mL EtOAc and wash three times with 50 mL of water. The organic layer was dried over MgSO$_4$, filtered and concentrated under reduced pressure to give a yellow solid. The solid was recrystallized from EtOAc/Hexanes to give the title compound as an orange solid (5.2 g, 60.5%). ES (−) MS m/e=344 (M−H).

1b) (S)-(+)-5-[1-(2-Methoxymethylpyrrolidinyl)sulfonyl]isatin

To a solution of 5-Chlorosulfonylisatin (0.5 g, 2.04 mmol) in 24 mL of 1:1 THF:CHCl$_3$ at 0° C. was added dropwise, via syringe pump, a solution of (S)-(+)-2-(Methoxymethyl) pyrrolidine (0.305 g, 2.65 mmol) and N,N-diisopropylethylamine (0.526 g, 4.08 mmol) in 4 mL of CHCl$_3$. The reaction was followed by TLC until complete (about 20 min). The solution was concentrated under reduced pressure to a small volume and purified by silica gel chromatography with 2, 3% CH$_3$OH/CH$_2$Cl$_2$ to give a yellow solid. The solid was then recrystallized from EtOAc/Hexanes to give the title compound as a yellow solid (0.205 g, 31%). ES (−) MS m/e=323 (M−H).

EXAMPLE 2

DL-5-[1-(2-(Hydroxyethyl)piperidinyl)sulfonyl] isatin

Prepared according to the procedure of example 1b) except using 2-(2-hydroxyethyl)piperidine, THF solely as the solvent, and purification by silica gel chromatography with 2, 3% CH$_3$OH/CH$_2$Cl$_2$ then preparative TLC chromatography with 10% CH$_3$OH/CH$_2$Cl$_2$ afforded the title compound as a yellow foam in 3.6% yield. ES (−) MS m/e=337 (M−H).

EXAMPLE 3

(+/−)-5-[1-(3-Hydroxymethyl)piperidinyl)sulfonyl] isatin

Prepared according to the procedure of example 1b) except using 3-(hydroxymethyl)piperidine and purification by silica gel chromatography with 3–6% CH$_3$OH/CH$_2$Cl$_2$ afforded the title compound as a yellow solid in 73% yield. ES (−) MS m/e=323 (M−H).

EXAMPLE 4

(S)-(+)-5-[1-(2-Hydroxymethylpyrrolidinyl)sulfonyl] isatin

Prepared according to the procedure of example 1b) except using 2-(hydroxymethyl)pyrrolidine and purification by silica gel chromatography with 3–5% CH$_3$OH/CH$_2$Cl$_2$ afforded the title compound as a yellow solid in 28% yield. ES (+) MS m/e=311 (M+H).

EXAMPLE 5

(S)-(+)-5-[1-(2-Benzyloxycarbonylpyrrolidinyl) sulfonyl]isatin

To a mixture of 5-Chlorosulfonylisatin (0.226 g, 0.922 mmol) and L-proline benzyl ester hydrochloride in 12 mL of 1:1 THF:CHCl$_3$ at 0° C. was added dropwise, via syringe pump, a solution of N,N-diisopropylethylamine (0.356 g, 2.76 mmol) in 1.5 mL of CHCl$_3$. The reaction was followed by TLC until complete (about 20 min). The solution was concentrated under reduced pressure to a small volume and purified by silica gel chromatography with 2% $CH_3OH/CH_2Cl_2$ to give the title compound as a yellow foam (0.305 g, 80%). ES (−) MS m/e=413 (M−H).

EXAMPLE 6

5-[N-(N-Methyl-2-hydroxyethylamino)sulfonyl]isatin

Prepared according to the procedure of example 1b) except using 2-(methylamino)ethanol and purification by silica gel chromatography with 2–3% $CH_3OH/CH_2Cl_2$ afforded the title compound as a yellow solid in 14% yield. ES (−) MS m/e=283 (M−H).

EXAMPLE 7

5-[N-(N-Methyl-2-(4-pyridine)ethylamino)sulfonyl]isatin

Prepared according to the procedure of example 1b) except using 4-(2-(methylamino)ethyl)pyridine and purification by silica gel chromatography with 2–3% $CH_3OH/CH_2Cl_2$. Upon standing 2 days in a solution of 3% $CH_3OH/CH_2Cl_2$ the title compound precipitated as a yellow solid in 17% yield. ES (−) MS m/e=344 (M−H).

EXAMPLE 8

5-[N-(N'-Benzylpiperazine)sulfonyl]isatin

Prepared according to the procedure of example 1b) except using N-benzylpiperizine and purification by silica gel chromatography with 1–2% $CH_3OH/CH_2Cl_2$ afforded the title compound as a yellow-brown foam in 39% yield. ES (−) MS m/e=384 (M−H).

EXAMPLE 9

(R)-(−)-5-[1-(2-Methoxymethylpyrrolidinyl)sulfonyl]isatin

Prepared according to the procedure of example 1b) except using (R)-(−)-2-(methoxymethyl)pyrrolidine and purification by silica gel chromatography with 2–3% $CH_3OH/CH_2Cl_2$, to give a yellow solid. The solid was then recrystallized from EtOAc to give the title compound as a yellow solid in 29% yield. ES (−) MS m/e=323 (M−H).

EXAMPLE 10

(S)-(+)-5-[1-(2-Methoxycarbonylpyrrolidinyl)sulfonyl]isatin

Prepared according to the procedure of example 5 except using L-proline methyl ester hydrochloride afforded the title compound as a yellow foam in 18% yield. ES(−) MS m/e=337 (M−H).

EXAMPLE 11

5-[N-(N-Methylanilino)sulfonyl]isatin

Prepared according to the procedure of example 1b) except using N-methylaniline, stirring overnight and purification by silica gel chromatography with 2% $CH_3OH/CH_2Cl_2$ afforded the title compound as a yellow foam in 9% yield. ES (−) MS m/e=315 (M−H).

EXAMPLE 12

(S)-(+)-5-[1-(2-t-Butoxycarbonylpyrrolidinyl)sulfonyl]isatin

Prepared according to the procedure of example 1b) except using L-proline t-butyl ester and purification by silica gel chromatography with 1–2% $CH_3OH/CH_2Cl_2$ afforded the title compound as an orange-yellow solid in 74% yield. ES (−) MS m/e=379 (M−H).

EXAMPLE 13

(S)-(+)-5-[1-(2-N,N-Dimethylaminocarbonylpyrrolidinyl)sulfonyl]isatin

Prepared according to the procedure of example 1b) except using N,N-dimethyl-L-prolinamide and purification by silica gel chromatography with 1–2% $CH_3OH/CH_2Cl_2$. Recrystallization from acetonitrile afforded the title compound as yellow needles in 45% yield. ES (−) MS m/e=350 (M−H).

EXAMPLE 14

(5)-(+)-5-[1-(2-Carboxypyrrolidinyl)sulfonyl]isatin

To (S)-(+)-5-[1-(2-t-butoxycarbonylpyrrolidinyl)sulfonyl]isatin (0.05 g, 0.13 mmol) was added 10 mL of a cooled solution of 5% water/TFA at 0° C. The resulting solution was warmed to room temperature and stirred 1 hour. The solution was concentrated in vacuo to give the title compound as a yellow solid (0.026 g, 60%). ES (−) MS m/e=323 (M−H).

EXAMPLE 15

(S)-(+)-1-Isopropyl-5-[1-(2-Methoxymethylpyrroidinyl)sulfonyl]isatin

To a solution of (S)-(+)-5-[1-(2-methoxymethypyrrolidinyl]isatin (0.11 g, 0.34 mmol) in 0.5 mL of DMF at 0° C. was added sodium hydride (0.016 g, 0.41 mmol) and the solution was warmed to room temperature. The resulting solution was stirred 5 min and isopropyl bromide (0.096 mL., 1.02 mmol) was added. The solution was heated at 60° C. for 4 hours. The reaction was quenched with water and extracted twice with $CH_2Cl_2$. The organic layer was dried over $MgSO_4$, filtered and concentrated under reduced pressure to give an oil. The oil was purified by preparative TLC silica gel chromatography with 5% $CH_3OH/CH_2Cl_2$ to give the title compound as a yellow solid (0.030 g, 24%). ES (+) MS m/e=367 (M+H).

EXAMPLE 16

5-[N-(N-Methyl-2-cyanoethylamino)sulfonyl]isatin

Prepared according to the procedure of example 1b) except using 3-methylaminopropionitrile and purification by silica gel chromatography with 2–5% $CH_3OH/CH_2Cl_2$. Recrystallization from EtOAc afforded the title compound as yellow solid in 8% yield. ES (−) MS m/e=292 (M−H).

EXAMPLE 17

(S)-(+)-5-[1-(2-(Anilinomethyl)pyrrolidinyl)sulfonyl]isatin

Prepared according to the procedure of example 1b) except using (S)-(+)-2-anilinomethylpyrrolidine and purification by silica gel chromatography with 2–3% $CH_3OH/CH_2Cl_2$. Recrystallization from EtOAc afforded the title compound as red crystals in 16% yield. ES (−) MS m/e=384 (M−H).

EXAMPLE 18

5-[N-(Ethoxycarbonylmethylamino)sulfonyl]isatin

Prepared according to the procedure of example 1b) except using N-methylglycine ethyl ester afforded the title compound as a yellow solid in 34% yield. ES (−) MS m/e=325 (M−H).

EXAMPLE 19

(+/−)-5-[1-(3-(N-Methyl-N-Box-amino)pyrrolidinyl) sulfonyl]isatin

Prepared according to the procedure of example 1b) except using 3-(N-methyl-N-Boc-amino)pyrrolidine and purification by silica gel chromatography with 2–3% $CH_3OH/CH_2Cl_2$ afforded title compound as a yellow solid in 83% yield. ES (−) MS m/e=408 (M−H).

EXAMPLE 20

(+/−)-5-[1-(3-(N-Methyl-N-phenethylcarbonylamino)pyrrolidinyl)sulfonyl]isatin 20a) (+/−)-5-[1-(3-(N-Methylamino)pyrrolidinyl)sulfonyl]isatin trifluoro acetic acid salt Prepared according to the procedure of example 14 except using (+/−)-5-[1-(3-(N-methyl-N-Boc-amino)pyrrolidinyl) sulfonyl]isatin afforded the title compound as a green oil. ES (+) MS m/e=310 (M+H).

20b) (+/−)-5-[1-(3-N-Methyl-N-phenethylcarbonylamino) pyrrolidinyl)sulfonyl]isatin To a solution of (+/−)-5-[1-(3-(N-methylamino) pyrrolidinyl)sulfonyl]isatin trifluoro acetic acid salt (0.065 g, 0.158 mmol) in 2 mL THF was added N,N-diisopropylethylamine (0.082 mL. 0.474 mmol) followed by hydrocinnamoylchloride (0.035 g, 0.206 mmol). The resulting solution was stirred for 20 minutes and then concentrated under reduced pressure. The residue was then purified by silica gel chromatography was 2–3% $CH_3OH/CH_2Cl_2$ followed by preparative TLC silica gel chromatography with 7% $CH_3OH/CH_2Cl_2$ to give the title compound as a yellow foam (0.016 g, 28% overall), ES (+) MS m/e=442 (M+H).

EXAMPLE 21

5-[N-(N-methyl-2-Methoxyethylamino)sulfonyl] isatin

Prepared according to the procedure of example 1b) except using 2-methoxyethylmethylamine and purification by silica gel chromatography with 3% $CH_3OH/CH_2Cl_2$ followed by recrystallization from EtOAc afforded the title compound as a red solid in 65% yield. ES (−) MS m/e=297 (M−H).

EXAMPLE 22

(S)-(+)-5-[1-(2-Phenoxymethylpyrrolidinyl)sulfonyl] isatin 22a) (S)-(+)-N-Boc-2-(2-Toluenesulfonyloxymethyl) pyrrolidine To a solution of (S)-(+)-N-Boc-2-Prolinol (3.51 g, 17.4 mmol) and pyridine (9.87 mL. 122 mmol) in 18 mL, of $CH_2Cl_2$ at 0° C. was added a solution of p-toluenesulfonylchloride in 20 mL $CH_2Cl_2$ dropwise. The solution was warmed to room temperature and stirred overnight. The solution was treated with 140 mL of water and extracted twice with 20 mL $CH_2Cl_2$. The organic layer was then dried over $Na_2SO_4$, filtered and concentrated under reduced pressure to give an oil. The oil was purified by silica gel chromatography with 20–25% EtOAc/Hexanes to give the title compound as a colorless oil (5.6 g, 90%). ES (+) MS m/e=256 (M+H).

22b) (S)-(+)-N-Boc-2-Phenoxymethylpyrrolidine

To a solution of phenol (0.40 g, 4,23 mmol) in 10 mL THF at 0° C. was added sodium hydride (0.226 g, 5.65 mmol) and the mixture was warmed to room temperature. The mixture was stirred 10 minutes until evolution of hydrogen ceased and cooled to 0° C. A solution of (S)-(+)-N-Box-2-(4-toluenesulfonyloxymethyl)pyrrolidine was added dropwise to the mixture and the resulting mixture was refluxed overnight. To the mixture was added 5 mL of DMF and the mixture was heated at 100° C. overnight. To the mixture was added EtOAc and the organic layer was washed thrice with water, thrice with 1N NaOH, and thrice with water. The organic layer was then dried over $MgSO_4$, filtered and concentrated under reduced pressure to give an oil. The oil was purified by silica gel chromatography with 7% EtOAc/Hexanes to give the title compound as a colorless oil (0.55 g, 71%. ES (+) MS m/e=278 (M+H).

22c) (S)-(+)-2-Phenoxymethylpyrrolidine

To a solution of (S)-(+)-N-Boc-2-phenoxymethylpyrrolidine (0.81 g. 2.9 mmol) in 5 mL of $CH_2Cl_2$ in 0° C. was added 5 mL of TFA dropwise over 1 hour. The solution was warmed to room temperature and stirred for 1.5 hours. The reaction mixture was slowly poured into 30 mL of 10% NaOH and extracted thrice with 20 mL $CH_2Cl_2$. The organic layer was then dried over $Na_2SO_4$, filtered and concentrated under reduced pressure to give a light yellow oil (0.41 g, 79%). ES (+) MS m/e=178 (M+H).

22d) (S)-(+)-5-[1-(2-Phenoxymethylpyrrolidinyl)sulfonyl] isatin

Prepared according to the procedure of example 1b) except (S)-(+)-2-phenoxymethylpyrrolidine afforded the title compound as a yellow solid in 46% yield. ES (+) MS m/e=387 (M+H).

EXAMPLE 23

(S)-(+)-5-[1-(2-Thiophenoxymethylpyrrolidinyl) sulfonyl]isatin 23a) (S)-(+)-N-Box-2-Thiophenoxymethylpyrrolidine To a solution of thiophenol (0.465 g, 4.23 mmol) in 10 mL THF at 0° C. was added sodium hydride (0.203 g, 5.08 mmol) and the mixture was warmed to room temperature. The mixture was stirred 10 minutes until evolution of hydrogen ceased and cooled to 0° C. A solution of (S)-(+)-2-(4-toluenesulfonyloxymethyl)pyrrolidine was added dropwise to the mixture and the resulting mixture was stirred overnight. To the mixture was added EtOAc and the organic layer was washed twice with water, twice with 1N NaOH, and twice with brine. The organic layer was then dried over $MgSO_4$, filtered and concentrated under reduced pressure to give an oil. The oil was purified by silica gel chromatography with 7% EtOAc/Hexanes to give the title compound as a colorless oil (0.67 g, 81%). ES (+) MS m/e=294 (M+H).

23b) (S)-(+)-2-Thiophenoxymethylpyrrolidine

Prepared according to the procedure of example 22c except using (S)-(+)-N-Boc-2-thiophenoxymethylpyrrolidine afforded the title compound as a light yellow oil (0.4 g, 91%). ES (+) MS m/e=194 (M+H).

23c) (S)-(+)-5-[1-(2-Thiophenoxymethylpyrrolidinyl) solfonyl]isatin

Prepared according to the procedure of example 1b) except (S)-(+)-2-thiophenoxymethylpyrrolidine afforded the title compound as a yellow solid in 32% yield. ES (+) MS m/e=403 (M+H).

EXAMPLE 24

(S)-(+)-5-[1-(2-Phenylaminocarbonylpyrrolidinyl) sulfonyl]isatin 24a) (S)-(+)-N-Boc-2-Phenylaminocarbonylpyrrolidine To a mixture of N-Boc-L-proline (1.0 g, 4.65 mmol), aniline (0.433 g. 4.65 mmol), and HOBT (0.753 g, 5.58 mmol) in 10 mL of $CH_2Cl_2$ was added EDC (1.07 g, 5.58 mmol) and the solution was stirred overnight. To the solution was added 70 mL of EtOAc and washed with 50 mL 3N HCl, 50 mL water, 50 mL $NaHCO_3$ (sat.), 50 mL 10% $K_2CO_3$, and 50 mL brine. The organic layer was then dried over $MgSO_4$, filtered and concentrated under reduced pressure to give a white solid (1.2 g. 89%. ES (+) MS m/e=291 (M+H).

24b) (S)-(+)-2-Phenylaminocarbonylpyrrolidine

To a solution of (S)-(+)-N-Boc-2-phenylaminocarbonylpyrrolidine (1.1 g, 3.8 mmol) in 5 mL of $CH_2Cl_2$ at 0° C. was added 5 mL of TFA dropwise over 1 hour. The solution was warmed to room temperature and stirred for 1.5 hours. To the reaction mixture was added 100 mL of water and the aqueous layer was washed with EtOAc. The aqueous layer was then made basic with 30 mL of 10% NaOH and extracted therein with 20 mL EtOAc. The organic layer was then dried over $Na_2SO_4$, filtered and concentrated under reduced pressure to give a white solid (0.40 g, 56%). ES (+) MS m/e=191 (M+H).

24c) (S)-(+)-5-[1-(2-Phenylaminocarbonylpyrrolidinyl) sulfonyl]isatin

Prepared according to the procedure of example 1b) except using (S)-(+)-2-phenylaminocarbonylpyrrolidine and purification by silica gel chromatography with 4% $CH_3OH/CH_2Cl_2$ afforded the title compound as a yellow solid in 56% yield. ES (−) MS n/e=398 (M−H).

EXAMPLE 25

(+/−)-5-[1-(3-Chloromethylpiperidinyl)sulfonyl] isatin

Prepared according to the procedure of example 1b) except using 3-chloromethylpiperidine (prepared according to the procedure of Balsamo et al. in *Eur. J. Med. Chem.* 29, 967, 1994) and purification by silica gel chromatography with 2% $CH_3OH/CH_2Cl_2$ afforded the title compound as a yellow solid in 30% yield. ES (+) MS m/e=41 (M−H).

EXAMPLE 26

5-[1-(4-Hydroypiperidinyl)sulfonyl]isatin

Prepared according to the procedure of example 1b) except using 4-hydroxypiperidine and purification by silica gel chromatography with 2% $CH_3OH/CH_2Cl_2$ afforded the title compound as a solid. ES(−) MS m/e=341 (M−H).

EXAMPLE 27

5-[N-(Morpholino)sulfonyl]isatin

A suspension of 5-[N-(morpholino)sulfonyl]-3,3-dichloro-2-oxindole (prepared in accompanying patent) (0.020 g. 0.057 mmol) in 3 mL of 3N HCl was reluxed for 2 hours. The mixture was diluted with water and extracted twice with $CH_2Cl_2$. The organic layer was dried over $CaCl_2$, filtered and concentrated under reduced pressure to give a yellow solid. The solid was purified by preparative TLC silica gel chromatography with 6% $CH_3OH/CH_2Cl_2$ to give the title compound as a yellow solid (0.011 g, 65%). ES (−) MS m/e=295 (M−H).

EXAMPLE 28

5-[N-(N-Methyl-2-phenethylamino)sulfonyl]isatin

To a mixture 5-[N-(N-methylphenethylamino)sulfonyl]-3,3-dichloro-2-oxindole (prepared in accompanying patent) (0.022 g, 0.057 mmol) in 2 mL of methanol was added 3 mL of 3N HCl and refluxed for 5 hours. The mixture was diluted with water and extracted twice with $CH_2Cl_2$. The organic layer was dried over $CaCl_2$, filtered and concentrated under reduced pressure to give a yellow solid. The solid was purified by preparative TLC silica gel chromatography with 6% $CH_3OH/CH_2Cl_2$ to give the title compound as a yellow solid (0.007 g, 37%). $^1$H NMR (400 MHz, $CDCl_3$) δ8.29 (s, 1H), 7.96 (s, 1H), 7.95 (d, 1H), 7.30–7.17 (m, 5H), 7.03 (d, 9.0 Hz, 1H), 3.32 (t, 7.3 Hz, 2H), 2.89 (t, 7.5 Hz, 2H), 2.81 (s, 3H).

EXAMPLE 29

(S)-(+)-1-Benzyl-5-[1-(2-thiophenoxymethylpyrrolidinyl)sulfonyl]isatin

Prepared according to the procedure of example 15) without hearing except using (S)-(+)-5-[1-(2-thiophenoxymethylpyrrolidinyl)sulfonyl]isatin and benzylbromide. Purification by silica gel chromatography with 2% $CH_3OH/CH_2Cl_2$ afforded the title compound as an orange oil in 86% yield. $^1$H NMR (400 MHz, $CDCl_3$) δ7.87 (d, 1.8 Hz, 1H), 7.76 (d, 8.5 Hz, 1H), 7.42–7.23 (m, 10H), 6.83 (d, 8.4 Hz, 1H), 4.95 (s, 3H), 3.64–3.49 (m, 3H), 3.09 (m, 1H), 2.76 (m, 1H), 1.95–1.61 (m, 4H).

EXAMPLE 30

(+/−)-5-[1-(3-(N-methylbenzamide)pyrrolidinyl) sulfonyl]isatin

Prepared according to the procedure of example 20b) except using benzoyl chloride afforded the title compound as a yellow solid in 47% yield. ES (+) MS M/e =414 (M+H).

EXAMPLE 31

5-[1-(2-(Phenylsulfinylmethyl)pyrrolidinyl)sulfonyl] isatin

To a solution of (S)-(+)-5-[1-(2-Thiophenoxymethylpyrrolidinyl)sulfonyl]isatin (0.064 g. 0.16 mmol) in 4 mL of 1:1 acetonitrile methylene chloride at 0° C. was added 80–85% 3-chloroperoxybenzoic acid (0.048 g, 0.24 mmol). The organic layer was concentrated under reduced pressure to give an oil. The oil was purified by silica gel chromatography with 2–3% $CH_3OH/CH_2Cl_2$ to give the title compound as a yellow oil (0.028 g, 42%). ES (+) MS m/e=419 (M+H).

EXAMPLE 32

5-[1-(azetidinyl)sulfonyl]isatin

Prepared according to the procedure of example 1b) except using azetidine and purification by silica gel chromatography with 2% $CH_3OH/CH_2Cl_2$ followed by recrystallization from EtOAc/Hexanes afforded the title compound as yellow needles. ES (−) MS m/e=265 (M−H).

EXAMPLE 33

(S)(+)-5-[1-(2-(4-Methylphenoxymethyl)pyrrolidinyl)sulfonyl]isatin 33a) (S)-(+)-N-Boc-2-(4-Methylphenoxymethyl)pyrrolidine To a solution of (S)-(+)-N-Boc-2-Prolinol (0.50 g. 2.5 mmol), 4-methylphenol (054 g, 5.0 mmol), and triphenylphosphine (1.3 g, 5.0 mmol) in 3.75 mL of THF at 0° C. was added a solution of dissopropyl azodicarboxylate (1.0 g, 5.0 mmol) in 2 mL THF dropwise. The solution was warmed to room temperature and stirred overnight. The solution was concentrated under reduced pressure and ethyl ether was added. The organic layer was washed twice with 50 mL of 1N NaOH, twice with 50 mL of water, twice with 50 mL 3N HCl, and once with 50 mL of water. The organic layer was then dried over $Na_2SO_4$, filtered and concentrated under reduced pressure to give an oil. The oil was purified by silica gel chromatography with 6% EtOAc/Hexanes to give the title compound as a colorless oil (0.094 g, 13%). ES (+) MS m/e=292 (M+H).

33b) (S)-(+)-2-(4-Methylphenoxymethyl)pyrrolidine

Prepared according to the procedure of example 22c) except using (S)-(+)-N-Boc-2-(4-Methylphenoxymethyl)pyrrolidine afforded the title compound as a light yellow oil (0.054 g, 87%). ES (+) MS m/e=192 (M+H).

33c) (S)-(+)-5-[1-(2-(4-Methylphenoxymethyl)pyrrolidinyl)sulfonyl]isatin

Prepared according to the procedure of example 1b) except using (S)-(+)-2-(4-Methylphenoxymethyl)pyrrolidine afforded by the title compound as a yellow solid in 59% yield. ES (−) MS m/e=399 (M−H).

EXAMPLE 34

(S)-(+)-5-[1-(2-(4-Methoxyphenoxymethyl)pyrrolidinyl)sulfonyl]isatin 34a) (S)-(+)-N-Boc-2-(4-Methoxyphenoxymethyl)pyrrolidine Prepared according to the procedure of example 33a) except using 4-methoxyphenol afforded the title compound as a colorless oil in 26% yield. ES (+) MS m/e=308 (M+H).

34b) (S)-(+)-2-(4-Methoxyphenoxymethyl)pyrrolidine

Prepared according to the procedure of example 23c) except using (S)-(+)-N-Boc-2-(4-Methoxyphenoxymethyl)pyrrolidine afforded the title compound as a light yellow oil inn 94% yield. ES (+) MS m/e=208 (M+H).

34c) (S)-(+)-5-[1-(2-(4-Methoxyphenoxymethyl)pyrrolidinyl)sulfonyl]isatin

Prepared according to the procedure of example 1b) except using (S)-(+)-2-(4-Methoxyphenoxymethyl)pyrrolidine afforded the title compound as an orange solid in 45% yield. ES (−) MS m/e=415 (M−H).

EXAMPLE 35

(S)-(+)-5-[1-(2-(4-Chlorophenoxymethyl)pyrrolidinyl)sulfonyl]isatin 35a) (S)-(+)-N-Boc-2-(4-Chlorophenoxymethyl)pyrrolidine Prepared according to the procedure of example 33a) except using 4-chlorophenol afforded the title compound as a colorless oil in 28% yield, ES (+) MS m/e=312 (M+H).

35b) (S)-(+)-2-(4-Chlorophenoxymethyl)pyrrolidine

Prepared according to the procedure of example 22c) except using (S)-(+)-N-Boc-2-(4-chloroyphenoxymethyl)pyrrolidine afforded the title compound as a light yellow oil in 99% yield. ES (+) MS m/e=212 (M+H).

35c) (S)-(+)-5-[1-(2-(4-Chlorophenoxymethyl)pyrrolidinyl)sulfonyl]isatin

Prepared according to the procedure of example 1b) except using (S)-(+)-2-(4-chlorophenoxymethyl)pyrrolidine afforded the title compound as a yellow solid in 16% yield. ES (−) MS m/e=419 (M−H).

EXAMPLE 36

(S)-(+)-5-[1-(2-(3,4-Dichlorophenoxymethyl)pyrrolidinyl)sulfonyl]isatin 36a) (S)-(+)-N-Boc-2-(3,4-Dichlorophenoxymethyl)pyrrolidine Prepared according to the procedure of example 33a) except using 3,4-dichlorophenol afforded the title compound as a colorless oil in 50% yield. ES (+) MS m/e=436 (M+H).

36b) (S)-(+)-2-(3,4-Dichlorophenoxymethyl)pyrrolidine

Prepared according to the procedure of example 22c) except using (S)-(+)-N-Boc-2-(3,4-dichlorophenoxymethyl)pyrrolidine afforded the title compound as a light yellow oil in 99% yield ES (+) MS m/e=246 (M+H).

36c) (S)-(+)-5-[1-(2-(3,4-Dichlorophenoxymethyl)pyrrolidinyl)sulfonyl]isatin

Prepared according to the procedure of example 1b) except using (S)-(+)-2-(3,4-dichlorophenoxymethyl)pyrrolidine afforded the title compound as a yellow solid in 39% yield. ES (−) MS m/e=453 (M−H).

EXAMPLE 37

5-[1-(2-(4-chlorophenoxy)azetidinyl)sulfonyl]isatin

Prepared according to the procedure of example 1b) except using 2-(4-chlorophenoxy)azetidine afforded the title compound as a yellow solid in 65% yield ES (−) MS m/e=391 (M−H).

EXAMPLE 38

5-[1-(Homopiperidinyl)sulfonyl]isatin

Prepared according to the procedure of example 1b ) except using homopiperidine afforded the title compound as an orange solid in 23% yield. ES (−) MS m/e=307 (M−H).

EXAMPLE 39

(S)-(+)-1-(3-Chlorobenzyl)-5-[1-(2-phenoxymetylpyrrolidinyl)sulfonyl]isatin

Prepared according to the procedure of example 15) without heating except using (S)-(+)-5-[1-(2-phenoxymethylpyrrolidinyl)sulfonyl]isatin and 3-chlorobenzylbromide. Purification by silica gel chromatography with 0–0.5% $CH_3OH/CH_2Cl_2$ afforded the title compound as an orange oil in 70% yield. ES (+) MS m/e=511 (M+H).

EXAMPLE 40

(S)-(+)-1-Benzyl-5-[1-(2-phenoxymethylpyrrolidinyl)sulfonyl]isatin

Prepared according to the procedure of example 15) without heating except using (S)-(+)-5-[1-(2-phenoxymethylpyrrolidinyl)sulfonyl]isatin and benzylbromide. Purification by silica gel chromatography with 0–0.5% $CH_3OH/CH_2Cl_2$ afforded the title compound as an orange oil in 81% yield. ES (+) MS m/e=477 (M+H).

EXAMPLE 41

5-[1-(Pyrrolidinyl)sulfonyl]isatin

Prepared according to the procedure of example 1b) except using pyrrolidine afforded the title compound as an orange solid in 8% yield. ES (−) MS m/e=279 (M−H).

EXAMPLE 42

(S)-(+)-1-(4-Methylbenzyl)-5-[1-(2-phenoxymethylpyrrolidinyl)sulfonyl]isatin

To a mixture of (S)-(+)-5-[1-(2-phenoxymethylpyrrolidinyl)sulfonyl]isatin (0.050 g. 0.13 mmol) and $K_2CO_3$ (0.045 g. 0.32 mmol) in 1.5 mL of DMF was added 4-methylbenzylbromide (0.36 g, 0.20 mmol). The mixture was allowed to stir overnight. Ethyl ether was added and the mixture was washed with water and acidified with 3N HCl. The organic layer was dried over $CaCl_2$, filtered and concentrated under reduced pressure to give an orange oil. Purification by silica gel chromatography with 0–1% $CH_3OH/CH_2Cl_2$ afforded the title compound as an orange oil in 75% yield. ES (+) MS m/e=491 (M+H).

EXAMPLE 43

(S)-(+)-1-(4-Chlorobenzyl)-5-[1-(2-phenoxymethylpyrrolidinyl)sulfonyl]isatin

Prepared according to the procedure of example 41) except using 4-chlorobenzylbromide afforded the title compound as an orange oil in 44% yield. ES (+) MS m/e=511 (M+H).

EXAMPLE 44

(S)-(+)-1-(3,4-Dichlorobenzyl)-5-[1-(2-phenoxymethylpyrrolidinyl)sulfonyl]isatin Prepared according to the procedure of example 42) except using 3,4-dichlorobenzylbromide afforded the title compound as an orange solid in 56% yield. ES (+) MS m/e=511 (M+H).

EXAMPLE 45

(S)-(+)-1-(2-Methylnaphthalene)-5-[1-(2-phenoxymethylpyrrolidinyl)sulfonyl]isatin Prepared according to the procedure of example 42) except using 2-(bromomethyl)naphthalene afforded the title compound as an orange foam in 84% yield. ES (+) MS m/e=527 (M+H).

EXAMPLE 46

(S)-(+)-1-[4-(1,2,3-Thiadiazole)benzyl]-5-[1-(2-phenoxymethylpyrrolidinyl)sulfonyl]isatin Prepared according to the procedure of example 42) except using 4-(1,2,3-thiadiazole)benzylbromide afforded the title compound as a yellow said in 55% yield. ES (+) MS m/e=561 (M+H).

EXAMPLE 47

(S)-(+)-1-Allyl-5-[1-(2-phenoxymethylpyrrolidinyl)sulfonyl]isatin

Prepared according to the procedure of example 42) except using alkylbromide afforded the title compound as an orange oil in 99% yield ES (+) MS m/e=427 (M+H).

EXAMPLE 48

(S)-(+)-1-(2-Phenylethyl)-5-[1-(2-phenoxymethylpyrrolidinyl)sulfonyl]isatin

Prepared according to the procedure of example 42) except using 2-phenylethylbromide and a catalytic amount of tetrabutylammonium iodide afforded the title compound as an orange foam in 71% yield. ES (+) MS m/e=491 (M+H).

EXAMPLE 49

(S)-(+)-1-(3-Phenylpropyl)-5-[1-(2-phenoxymethylpyrrolidinyl)sulfonyl]isatin

Prepared according to the procedure of example 42) except using 3-phenylpropylbromide and a catalytic amount of tetrabutylammonium iodide afforded the title compound as an orange foam in 83% yield. ES (+) MS m/e=505 (M+H).

EXAMPLE 50

(S)-(+)-1-(4-Methoxybenzyl)-5-[1-(2-phenoxymethylpyrrolidinyl)sulfonyl]isatin

Prepared according to the procedure of example 42) except using 4-methoxybenzylbromide afforded the title compound as yellow solid in 86% yield. ES (+) MS m/e=507 (M+H).

EXAMPLE 51

(S)-(+)-1-Cyclohexylmethyl-5-[1-(2-phenoxymethylpyrrolidinyl)sulfonyl]isatin

Prepared according to the procedure of example 15) except using (S)-(+)-5-[1-(2-phenoxymethylpyrrolidinyl)sulfonyl]isatin and cyclohexylmethyl bromide and heating at 70° C. overnight. Purification by silica gel chromatography with $CH_2Cl_2$ afforded the title compound as yellow solid in 32% yield. ES (+) MS m/e=483 (M+H).

EXAMPLE 52

(S)-(+)-1-Methyl-5-[1-(2-phenoxymethylpyrrolidinyl)sulfonyl]isatin

Prepared according to the procedure of example 42) except using iodomethane afforded the title compound as an orange solid in 81% yield. ES (+) MS m/e=401 (M+H).

EXAMPLE 53

(S)-(+)-1-(3-Iodobenzyl)-5-[1-(2-phenoxymethylpyrrolidinyl)sulfonyl]isatin

Prepared according to the procedure of example 42) except using 3-iodobenzylbromide afforded the title compound as a yellow foam in 67% yield. ES (+) MS m/e=603 (M+H).

EXAMPLE 54

(S)-(+)-1-Methyl-5-[1-(2-(N-methylanilinomethyl)pyrrolidinyl)sulfonyl]isatin

Prepared according to the procedure of example 42) except using an excess of iodomethane afforded the title compound as a red foam in 66% yield. ES (+) MS m/e=414 (M+H).

EXAMPLE 55

(S)-(+)-1-(t-Butoxycarbonylmethyl)-5-[1-(2-phenoxymethylpyrrolidinyl)sulfonyl]isatin Prepared according to the procedure of example 42) except using t-butylbromoacetate afforded the title compound as an orange oil in 79% yield. ES (+) MS m/e=546 (M+HCO.H).

EXAMPLE 56

(S)-(+)-1-(Acetic acid)-5-[1-(2-phenoxymethylpyrrolidinyl)sulfonyl]isatin

To a solution of (S)-(+)-1-(t-butoxycarbonylmethyl)-5-[1-(2-phenoxymethylpyrrolidinyl)sulfonyl]isatin (0.052 g, 0.104 mmol) in 5 mL of $CH_2Cl_2$ at 0° C. was added 5 mL of TFA. The solution was warmed to room temperature and stirred for 1.5 hours. The organic layer was concentrated under reduced pressure and redissolved in $CH_2Cl_2$ and toluene was added. The organic layer was concentrated under reduced pressure to give an oil. The oil was purified by silica gel chromatography with 3% $CH_3OH/CH_2Cl_2$ and 1% acetic acid to give the title compound as an orange oil (0.029 g, 63%). ES (+) MS m/e=(M+H).

EXAMPLE 57

(S)-(+)-1-Methyl-5-[1-(2-(anilinomethyl)pyrrolidinyl)sulfonyl]isatin

Prepared according to the procedure for example 15) without heating except using (S)-(+)-5-[1-(2-(Anilinomethyl)pyrrolidinyl)sulfonyl]isatini and 0.9 equivalents of iodomethane. Purification by silica gel chromatography with 0.5% $CH_3OH/CH_2Cl_2$ afforded the title compound as an orange oil in 85% yield. ES (+) MS m/e=400 (M+H).

EXAMPLE 58

(R)-(−)-5-[1-(2-(anilinomethyl)pyrrolidinyl)sulfonyl]isatin

58a) D-N-Boc-Proline anilide

To a solution of D-N-Boc-proline (2.0 g, 9.3 mmol), aniline (0.87 g, 9.4 mmol), and 1-hydroxybenzotriazole hydrate (1.5 g, 11 mmol) in 20 mL of methylene chloride at 0° C. was added 1-(3-dimethylaminopropyl)-3-ethylcarbodiimide hydrochloride (2.1 g, 11 mmol) and the resulting solution was stirred at room temperature overnight. The solution was washed with 100 mL of 3N HCl and the aqueous layer was extracted with methylene chloride. The combined organic layers were dried over magnesium sulfate, filtered and concentrated under reduced pressure to give the title compound as white solid. ES (+) MS m/e=291 (M+H)

58b) D-Proline anilide

Prepared according to the procedure of example 56) except D-N-Boc-Proline anilide. Purification by silica gel chromatography with 90:9:1 $EtOAc:CH_3OH:NH_4OH$ afforded the title compound as a white solid (68% yield from 57a), ES (+) MS m/e=191 (M+H).

58c) (R)-2-(anilinomethyl)pyrrolidine

To a solution of D-Proline anilide (1.15 g, 6.0 mmol) in 20 mL of THF at 0° C. was added a 1 M solution of lithium aluminum hydride (14 mL, 14 mmol) in THF. The resulting solution was stirred at 0° C. for 11 hours. The reaction was carefully quenched with a saturated solution of $Na_2SO_4$ and extracted with EtOAc. The organic layer was dried over sodium sulfate, filtered and concentrated under reduced pressure to give the title compound as an oil. The oil was purified by silica gel chromatography with 3% $CH_3OH/CH_2Cl_2$ and 1% triethyl amine to give the title compound as a yellow oil (0.029 g, 63%). ES (+) MS m/e=177 (M+H)

58d) (R)-(−)-5-[1-(2-(anilinomethyl)pyrrolidinyl)sulfonyl]isatin

Prepared according to the procedure of example 1b) except using (R)-2-(anilinomethyl)pyrrolidine and purification by silica gel chromatography with 2–3% $CH_3OH/CH_2Cl_2$ afforded the title compound as an orange solid in 78% yield. ES (+) MS m/e=386 (M+H).

EXAMPLE 59

(S)-(+)-1-Benzyl-5-[1-(2-anilinomethyl)pyrrolidinyl)sulfonyl]isatin

Prepared according to the procedure of example 15) without heating except using (S)-(+)-5-[1-(2-Anilinomethyl)pyrrolidinyl)sulfonyl]isatin and 1.1 equivalents of benzyl bromide. Purification by silica gel chromatography with 0.5% $CH_3OH/CH_2Cl_2$ afforded the title compound as an orange oil in 52% yield. ES (+) MS m/e=476 (M+H).

EXAMPLE 60

(S)-(+)-1-Cyanomethyl-5-[1-(2-phenoxymethylpyrrolindinyl)sulfonyl]isatin

Prepared according to the procedure of example 42) except using iodoacetonitrile afforded the title compound as a yellow foam in 39% yield. ES (−) MS m/e=424 (M−H).

EXAMPLE 61

(S)-(+)-1-[2-(2-Ethyl)-1-methylpyrrolidine]-5-[1-(2-phenoxymethylpyrrolindinyl)sulfonyl]isatin Prepared according to the procedure of example 42) except using 2-(2-chloroethyl)-1-methylpyrrolidine and a catalytic amount of tetrabutylammonium iodide afforded the title compound as a yellow foam in 38% yield. ES (+) MS m/e=498 (M+H).

EXAMPLE 62

(S)-(+)-1-(3-Methylsulfonylbenzyl)-5-[1-(2-phenoxymethylpyrrolidinyl)sulfonyl]isatin Prepared according to the procedure of example 42) except using 3-methylsulfonylbenzyl bromide afforded the title compound as a yellow foam in 42% yield. ES (+) MS m/e=555 (M+H).

EXAMPLE 63

(S)-(+)-1-(3-Carboxamidobenzyl)-5-[1-(2-phenoxymethylpyrrolidinyl)sulfonyl]isatin Prepared according to the procedure of example 42) except using 3-carboxyamidobenzyl chloride afforded the title compound as a yellow solid in 19% yield. ES (+) MS m/e=520 (M+H).

EXAMPLE 64

(R)-5-[1-(2-Phenethylpyrrolindinyl)sulfonyl]isatin 64a) (S)-(+)-N-Boc-2-Prolinal To a solution of DMSO (5.86 mL, 75.8 mmol) in 120 mL of $CH_2Cl_2$ at −78° C. was added oxalyl chloride (4.40 mL, 50.4 mmol) dropwise. The solution was stirred 10 min and then a solution of (S)-(+)-N-Boc-2-Prolinol (5.08 g, 25.2 mmol) in 50 mL of $CH_2Cl_2$ was added dropwise. The solution was stirred 20 min and triethylamine (14.1 mL, 100 mmol) was added dropwise. The solution was warmed to room temperature and then stirred for 30 min. The solution was treated with 50 mL of water and extracted twice with 100 mL $CH_2Cl_2$. The organic layer was then dried over Na$_2$SO$_4$, filtered and concentrated under reduced pressure to give an oil. The oil was purified by silica gel chromatography with 25% EtOAc/Hexanes to give the title compound as a light yellow oil (5.0 g, 99%) ES (+) MS m/e=200 (M+H).

64b) (S)-(+)-N-Boc-2-Styrylpyrrolidine

To a suspension of sodium hydride (0.241 g, 6.03 mmol) in 27 mL of toluene was added benzyltriphenylphosphonium chloride (2.35 g, 6.03). The solution was heated at 60° C. for 10 min and cooled to room temperature. The solution was treated with (S)-(+)-N-Boc-2-prolinal (1.0 g, 5.03 mmol). After the evolution of hydrogen, the solution was refluxed for 3 h. The solution was treated with 3 N HCl and extracted twice with EtOAc. The organic layer was then dried over MgSO$_4$, filtered and concentrated under reduced pressure to give an oil. The oil was purified by silica gel chromatography with 25% EtOAc/Hexanes to give the title compound as a light yellow oil (0.56 g, 41%). ES (+) MS m/e=274 (M+H).

64c) (S)-(+)-N-Boc-2-phenethylpyrrolidine

To a solution of (S)-(+)-N-Boc-2-styrylpyrrolidine (0.56 g, 2.1 mmol) in 10 mL of methanol was added a catalytic amount of 10% Pd/C. The mixture was hydrogenated on a Parr shaker at 50 psi for 5 h. The mixture was filtered and the solution was concentrated under reduced pressure to give the title compound as a light yellow oil (0.53 g, 95%). ES (+) MS m/e=276 (M+H).

64d) (S)-(+)-2-phenethylpyrrolidine

To a solution of (S)-(+)-N-Boc-2-phenethylpyrrolidine (0.53 g, 1.93 mmol) in 5 mL of CH$_2$Cl$_2$ at 0° C. was added 5 mL of TFA. The solution was warmed to room temperature and stirred for 3 hours. The organic layer was concentrated under reduced pressure and redissolved in CH$_2$Cl$_2$. The organic layer was washed with 1 M NaOH, dried over Na$_2$SO$_4$, filtered and concentrated under reduced pressure to give the title compound as a light yellow oil (0.31 g, 91%). ES (+) MS m/e=176 (M+H).

64e) (R)-5-[1-(2-Phenethylpyrrolidinyl)sulfonyl]isatin

Prepared according to the procedure of example 1b) except using (R)-2-phenethylpyrrolindine and purification by silica gel chromatography with 50% EtOAc/Hexanes to afford the title compound as an orange solid 44.3% yield. ES (−) MS m/e=383 (M−H).

EXAMPLE 65

5-[1-(2-Phenoxymethylpiperdinyl)sulfonyl]isatin 65a) 2Phenoxymethylpyridine

To a mixture of phenol (5.25 g, 55.8 mmol) and 2-chloromethylpyridine hydrochloride (10 g, 61.0 mmol) in 80 mL of toluene was added sodium hydroxide (5.35 g, 134 mmol. The mixture was refluxed for 16 hours. The mixture was washed twice with 60 mL of water. The organic layer was then extracted three times with 25 mL of 6 N HCl. The aqueous layer was made basic with 250 mL of 10% NaOH and extracted three times with 150 mL of CH$_2$Cl$_2$. The organic layer was dried over Na$_2$SO$_4$, filtered and concentrated under reduced pressure to give the title compound as a yellow oil (10.6 g, 94%). ES (+) MS m/e=186 (M+H).

65b) 2-Phenoxymethylpiperdine

To a solution of 2-phenoxymethylpyridine (1.0 g, 5.4 mmol) in 23 mL of acetic acid was added 0.13 g of 5% Pt/C. The mixture was hydrogenated on a Parr shaker at 50 psi for 5 h. Toluene and EtOAc were added to the mixture and it was filtered and concentrated under reduced pressure to give an oil. The oil was dissolved in CH$_2$Cl$_2$ and washed with 10% NaOH. The organic layer was dried over Na$_2$SO$_4$, filtered and concentrated under reduced pressure to give a 50/50 mixture of the title compound and starting material as a yellow oil (1.0 g, 98%). ES (+) MS m/e=192 (M+H).

65c) 5-[1-(2-Phenoxymethylpiperdinyl)sulfonyl]isatin

Prepared according to the procedure of example 1b) except using 2-phenoxymethylpiperidine and purification by silica gel chromatography with 25–50% EtOAc/Hexanes to afford the title compound as a yellow solid 65.7% yield. ES (−) MS m/e=399 (M−H).

EXAMPLE 66

(S)-5-[1-(1-Methoxy-2-phenethylpyrrolidinyl) sulfonyl]isatin

66a) N-Boc-2-(1-Hydroxy-2-phenethyl)pyrrolidine

To a solution of (S)-(+)-N-Boc-2-Prolinal (1.0 g, 5.03 mmol) in 20 mL of THF at 0° C. was added 2.0 M benzylmagnesium chloride (2.51 mL, 5.03 mmol) in THF dropwise. The solution was warmed to room temperature and stirred for 2 days. The solution was treated with 1 M HCl and extracted twice with EtOAc. The organic layer was then dried over Na$_2$SO$_4$, filtered and concentrated under reduced pressure to give an oil. The oil was purified by silica gel chromatography with 25–44% EtOAc/Hexanes to give the title compound as a colorless oil (0.65 g, 45%). ES (+) MS m/e=292 (M+H).

66b) N-Boc-2-(1-Methoxy-2-phenethyl)pyrrolidine

To a solution of N-Boc-2-(1-hydroxy-2-phenethyl) pyrrolidine (0.27 g, 0.91 mmol) in 3 mL and iodomethane (1.3 g, 9.1 mmol) at 0° C. was added sodium hydride (0.37 g, 9.1 mmol) and the mixture was stirred for 1 hour. The mixture was cautiously treated with water and extracted with EtOAc. The organic layer was then dried over Na$_2$SO$_4$, filtered and concentrated under reduced pressure to give an oil. The oil was purified by silica gel chromatography with 5% EtOAc/Hexanes to give the title compound as a colorless oil (0.18 g, 65%). ES (+) MS m/e=306 (M+H)ds 66c) 2-(1-Methoxy-2-phenethyl)pyrrolidine Prepared according to the procedure of example 62d) except N-Boc-2-(1-Methoxy-2-phenethyl)pyrrolidine afforded the title compound as a yellow oil in 99% yield. ES (+) MS m/e=206 (M+H).

66d) (S)-5-[1-(1-Methoxy-2-phenethylpyrrolidinyl) sulfonyl]isatin

Prepared according to the procedure of example 1b) except using 1-methoxy-2-phenethylpyrrolidine and purification and purification by silica gel chromatography with 50% EtOAc/Hexanes to afford the title compound as an orange solid in 41.5% yield. ES (−) MS m/e=413 (M−H).

EXAMPLE 67

(S)-1-(4-Pyridinylmethyl)-5-[1-(2-phenoxymethylpyrrolidinyl)sulfonyl]isatin 67a) 4-bromomethyl pyridine hydrobromide To a solution of 4-pyridylcarbinol (3 g, 27.5 mmol) in 30 mL of CHCl$_3$ was added phosphorus pentabromide (5.93 g, 13.7 mmol). The solution was refluxed for 1 hour. The solvent was removed in vacuo and recrystallized in ethanol to afford the title compound as a white solid (4.05 g, 58.1%). ES (+) MS m/e=173 (M+H).

67b) (S)-1-(4-Pyridinylmethyl)-5-[1-(2-phenoxymethylpyrrolidinyl)sulfonyl]isatin Prepared according to the procedure of example 15) except using 4-bromomethyl pyridine hydrobromide and purification by silica gel chromatography with 50–80% EtOAc/Hexanes to afford the title compound as a yellow solid in 18% yield. ES (+) MS m/e=478 (M+H).

EXAMPLE 68

(S)-1-(3-Pyridinylmethyl)-5-[1-(2-phenoxymethylpyrrolindinyl)sulfonyl]isatin 68a) 3-bromomethyl pyridine hydrobromide To 3-pyridylcarbinol (2 g, 18.3 mmol) was added 47–49% hydrobromic acid (2 mL, 13.7 mmol). The solution was refluxed for 3 hours. The solution was diluted with EtOAc and extracted thrice with EtOAc. The organic layer was dried over MgSO$_4$, filtered and concentrated under reduced pressure to give a solid. The solid was recrystallized in ethanol to afford the title compound as a white solid (2.13 g, 45.8%). ES (+) MS m/e=173 (M+H).

68b) (S)-1-(3-Pyridinylmethyl)-5-[1-(2-phenoxymethylpyrrolindinyl)sulfonyl]isatin Prepared according to the procedure of example 15) except using 3-bromomethyl pyridine hydrobromide and purification by silica gel chromatography with 50% EtOAc/Hexanes to afford the title compound as a yellow solid in 29% yield. ES (+) MS m/e=478 (M+H).

EXAMPLE 69

5-[1-(N-Acetylhomopiperazine)sulfonyl]isatin

Prepared according to the procedure of example 1b) except using N-acetylhomopiperazine and purification by silica gel chromatography with 75% EtOAc/Hexanes to afford the title compound as a yellow solid in 19% yield. ES (+) MS m/e=352 (M+H).

EXAMPLE 70

5-[1-(Thiazolidine)sulfonyl]isatin

Prepared according to the procedure of example 1b) except using thiazolidine and purification by silica gel chromatography with 50% EtOAc/Hexanes to afford the title compound as a yellow solid in 14% yield. ES (−) MS m/e=297 (M+H).

EXAMPLE 71

5-[1-(4-Piperanoylpiperazine)sulfonyl]isatin

Prepared according to the procedure of example 1b) except using 1-piperanoylpiperazine and purification by silica gel chromatography with 25–40% EtOAc/Hexanes to afford the title compound as a yellow solid in 19% yield. ES (+) MS m/e=430 (M+H).

EXAMPLE 72

(S)-1-[3-(t-Butoxycarbonyl)benzyl]-5-[1-(2-phenoxymethylpyrrolindinyl)sulfonyl]isatin 72a) t-Butyl 3-(bromomethyl)benzoate To a solution of 3-chloromethylbenzoic acid (0.500 g, 2.9 mmol) in 10 mL of CH$_3$Cl$_2$ was added t-butyl-2,2,2-trichloroacetimidate (1.28 g, 5.8 mmol) in 2 mL of cyclohexane and boron trifluoride diethyl etherate (58 µL, 0.47 µmol). The solution was stirred for 18 hours, then an excess of NaHCO$_3$ was added and the solution was stirred for another 10 minutes. The solution was filtered through a silica plug. Removal of the solvent in vacuo afforded the title compound as a white solid (0.355 g, 53%). ES (+) MS m/e=227 (M+H).

72b) (S)-1-[3-(t-Butoxycarbonyl)phenylmethyl]-5-[1-(2-phenoxymethylpyrrolindinyl)sulfonyl]isatin Prepared according to the procedure of example 15) except using t-butyl 3-chloromethylbenzoate and purification by silica gel chromatography with 25% EtOAc/Hexanes to afford the title compound as a yellow solid in 32% yield. ES (+) MS m/e=577 (M+H).

EXAMPLE 73

(S)-1-(3-Carboxyphenylmethyl)-5-[1-(2-phenoxymethylpyrrolidinyl)sulfonyl]isatin

Prepared according to the procedure of example 56) except using (S)-1-[3-(t-Butoxycarbonyl)phenylmethyl]-5-[1-(2-phenoxymethylpyrrolidinyl)sulfonyl]isatin and purification by silica gel chromatography with 2% MeOH/CH$_2$Cl$_2$ and 1% acetic acid to afford the title compound as a yellow oil in 75% yield. ES (+) MS m/e=521 (M+H).

EXAMPLE 74

5-[1-(4-Acetyl-(2-thiophene)-homopiperazine)sulfonyl]isatin

Prepared according to the procedure of example 1b) except using 1-acetyl-(2-thiophene)-homopiperazine and purification by silica gel chromatography with 75% EtOAc/Hexanes to afford the title compound as a yellow solid in 24.6% yield. ES (+) MS m/e=420 (M+H).

EXAMPLE 75

(S)-1-(4-Cyanophenylmethyl)-5-[1-(2-phenoxymethylpyrrolidinyl)sulfonyl]isatin

Prepared according to the procedure of example 41) except using α-bromo-p-toluidine and purification by silica gel chromatography with 75% EtOAc/Hexanes to afford the title compound as an orange solid in 30.8% yield. ES (+) MS m/e=352 (M+H).

EXAMPLE 76

(S)-1-(3,4-Methylenedioxybenzyl)-5-[1-(2-phenoxymethylpyrrolidinyl)sulfonyl]isatin Prepared according to the procedure of example 42) except using 3,4-methylenedioxybenzyl chloride and purification by silica gel chromatography with 25% EtOAc/Hexanes to afford the title compound as an orange solid in 40% yield. ES (+) MS m/e=521 (M+H).

EXAMPLE 77

(S)-1-(Methoxymethyl)-5-[1-(2-phenoxymethylpyrrolidinyl)sulfonyl]isatin

Prepared according to the procedure of example 15) except using Methoxymethylbromide and purification by silica gel chromatography with 25% EtOAc/Hexanes to afford the title compound as an orange solid in 64.6% yield. ES (+) MS m/e=431 (M+H).

EXAMPLE 78

(S)-1-[3-(t-Butoxycarbonyl)propyl]-5-[1-(2-phenoxymethylpyrrolindinyl)sulfonyl]isatin 78a) t-Butyl-3-bromopropionoate To a pressure tube with a solution of 3-boromopropanic acid (1.0 g, 6.5 mmol) in 4 mL of Et$_2$O was added a drop of H$_2$SO$_4$. The solution was cooled to −20° C. and 2-methylpropene (3 mL, 53.4 mmol) was slowly bubbled into the solution. The pressure tube was sealed and allowed to warm room temperature. The mixture stirred for 18 hours.

The solution was cooled back to −20° C. and the seal was removed. The solution was washed twice with water and twice with 10% NaHCO$_3$. The organic layer was dried with MgSO$_4$ and removed in vacuo to afford the title compound as a clear oil (0.700 g, 70%). ES (+) MS m/e=210 (M+H).
73b) (S)-1-[3-(t-Butoxycarbonyl)propyl]-5-[1-(2-phenoxymethylpyrrolindinyl)sulfonyl]isatin Prepared according to the procedure of example 15)except using t-butyl-3-bromopropionate and purification by silica gel chromatography with 40–50% EtOAc/Hexanes to afford the title compound as a yellow solid in 23.4% yield. ES (+) MS m/e=577 (M+H).

EXAMPLE 79

(S)-1-(3-Carboxypropyl)-5-[1-(2-phenoxymethylpyrrolindinyl)sulfonyl]isatin

Prepared according to the procedure of example 56) except using (S)-1-[3-(t-butoxycarbonyl)propyl]-5-[1-(2-phenoxymethylpyrrolidinyl)sulfonyl]isatin and purification by silica gel chromatography with 2% MeOH/CH$_2$Cl$_2$ and 1% acetic acid to afford the title compound as a yellow oil in 75% yield. ES (+) MS m/e=521 (M+H).

EXAMPLE 80

(S)-1-[4-(t-Butoxycarbonyl)phenylmethyl]-5-[1-(2-phenoxymethylpyrrolindinyl)sulfonyl]isatin
80a) t-Butyl 4-(bromomethyl)benzoate Prepared according to the procedure of example 72) except using 4-chloromethylbenzoic acid and purification by silica gel chromatography with 25% EtOAc/Hexanes to afford the title compound as a white solid 97% yield. ES (+) MS m/e=227 (M+H).
80b) (S)-1-[4-(t-Butoxycarbonyl)phenylmethyl]-5-[1-2-phenoxymethylpyrrolidinyl)sulfonyl]isatin Prepared according to the procedure of example 15) except using t-butyl 4-(bromomethyl)benzoate and purification by silica gel chromatography with 40–50% EtOAc/Hexanes to afford the title compound as a yellow solid in 23.4% yield. ES (+) MS m/e=577 (M+H).

EXAMPLE 81

(S)-1-(4-Carboxyphenylmethyl)-5-[1-(2-phenoxymethylpyrrolindinyl)sulfonyl]isatin Prepared according to the procedure of example 56) except using (S)-1-[4-(t-butoxycarbonyl)phenylmethyl]-5-[1-(2-phenoxymethylpyrrolidinyl)sulfonyl]isatin and purification by silica gel chromatography with 2% MeOH/CH$_2$Cl$_2$ and 1% acetic acid to afford the title compound as a yellow oil in 64.2% yield. ES (−) MS m/e=519 (M−H).
Preparation of Active Caspase 3

Full length Caspase 3 was expressed intracellularly in *E.coli* with N-terminal hexa his tag. *E coli* cells were lysed in 10 ml/g of cells of lysis buffer (50 mM Na phosphate pH 7.2 0.1 M NaCl, 0.1% Tween 20, and 10 mM b-mercaptoethanol) using Microfluidics M110Y homogenizer at 10,000 psi. After centrifugation, Caspase 3 activity was detected in lysate supernatant. The supernatant was buffer-exchanged on Sephadex G25 column equilibrated with 20 mM TrisHCl. 10% Sucrose, 0.1% CHAPS, 2 mM DTT, pH 7.8 (TSCD). Fractions containing Caspase 3 activity was applied to DEAE Toyopearl 650 M (Supelco Inc) equilibrated with Buffer TSCD. The column was eluted with a linear gradient of 20 mM to 120 mM of Tris HCl pH 7.8 in TSCD. Caspase 3 was eluted in early of the gradient before the majority of impurities eluted. This partially purified Capase 3 was used for inhibitor screening. All operations were performed at 4° C. and Caspase activity was measured using substrate. DEVD-AMC, and Cynatach Fluolite 1000 plate reader.
Capase 3 Inhibition Assay Capase 3 was assayed at 30 degrees C. in 96-well plates using the fluorogenic tetrapeptide substrate N-acetyl-L-aspartyl-L-glutamyl-L-valyl-L-aspartyl-7-amido-4-methylcoumarin (Ac-DEVD-AMC). The assays were conducted at pH 7.5 in a buffered system containing 25 mM Hepes, 10% sucrose, 0.1% CHAPS, and 1–50 uM DTT. The concentration of substrate was fixed at 10 uM. Fluorescence of the liberated 7-amino-4-methylcoumarin was continuously monitored at 460 nm following excitation at 360 nm.
Compound Testing Compounds were tested at a single dose of 50 to 100 uM. Activity was monitored as described above over a 30 to 60-minute time period following the simultaneous addition of substrate and inhibitor to enzyme to initiate the reaction. The progress curves thus generated were fit by computer to Eq. 1 in order to assess potency and/or time-dependency:

$$v = \frac{(V_o(1 - e^{-k_{obs}t})}{k_{obs}} \quad (1)$$

Representative compounds of formula (I) have demonstrated positive inhibitory activity in the above noted assay.
Apoptosis Assay (Jurkat Cells):
Materials:Compounds Compounds were made as stocks (5–100 mM) in dimethylsulfoxide (DMSO) and diluted in DMSO to provide final concentrations, with DMSO concentrations ranging from 0.1–1%.
Preparation of cells Jurkat cells were obtained from American Type Culture Collection and grown in RPMI-1640 media supplemented with 10% fetal bovine serum at 37°, 5% CO$_2$. Cells were seeded in T-flasks at 0.03 to 0.08×10$^6$ cells/ml and used for experiments at 0.5 to 1.0×10$^6$ cells/ml. Other proliferative cells can be used with apoptosis induced by anti-fas, camptothecine, cerimeide of TNF.
Apoptosis Assay A method for measuring apoptosis is to quantitate the amount of broken DNA fragments using a fluorescent end-labeling method, a system used in the ApopTag kit from Oncor (Gaithersburg, Md.). In brief, the enzyme terminal deoxynucleotidyl transferase extends the DNA fragments with digoxigenin-containing nucleotides, which are then dected with an antidigoxigenin antibody carrying fluorescein to allow detection by fluorescence (494 nm excitation and 523 nm emission). Propidium iodide is used as counter stain to measure total DNA content. Flow cytometric analysis was done on Becton-Dickonson (Rutherfor, N.J.) FACSan instrument using CellQuest software.

METHODS OF TREATMENT

For therapeutic use the compounds of the present invention will generally be administered in a standard pharmaceutical composition obtained by admixture with a pharmaceutical carrier or diluent selected with regard to the intended route of administration and standard pharmaceutical practice. For example, they may be administered orally in the form of tablets containing such excipients as starch or lactose, or in capsule, ovules or lozenges either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood. The choice of form for administration as well as effective dosages will vary depending, inter alia, on the condition being treated. The choice of mode of administration and dosage is within the skill of the art.

The compounds of the present invention, particularly those noted herein or their pharmaceutically acceptable salts which are active when given orally, can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerin, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Preferably the composition is in unit dose form such as a tablet or capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

A typical suppository formulation comprises a compound or a pharmaceutically acceptable salt thereof which is active when administered in this way, with a binding and/or lubricating agent such as polymeric glycols, gelatins or cocoa butter or other low melting vegetable or synthetic waxes or fats.

The pharmaceutically acceptable compounds of the invention will normally be administered to a subject in a daily dosage regimen. For a patient this may be, for example, from about 0.001 to about 100 mg/kg, preferably from about 0.001 to about 10 mg/kg animal body weight. A daily dose, for a larger mammal is preferably from about 1 mg to about 1000 mg, preferably between 1 mg and 500 mg or a pharmaceutically acceptable salt thereof, calculated as the free base, the compound being administered 1 to 4 times per day. Unit dosage forms may contain from about 25 µg to about 500 mg of the compound.

There are many diseases and conditions in which dysregulation of apoptosis plays an important role. All of these conditions involve undesired, deleterious loss of specific cells with resulting pathological consequences.

Bone remodeling involves the initial resorption by osteoclasts, followed by bone formation by osteoblasts. Recently, there have been a number of reports of apoptotic events occurring during this process. Apoptotic events have been observed in both the bone forming and bone resorbing cells in vitro and indeed at the sites of these remodeling units in vivo.

Apoptosis has been suggested as one of the possible mechanisms of osteoclast disappearance from reversal sites between resorption and formation. TGF-β1 induces apoptosis (approx. 30%) in osteoclasts of murine bone marrow cultures grown for 6 days in vitro. (Hughes, et al., *J. Bone Min. Res.* 9, S138 (1994)). The anti-resorptive bisphosphonates (clodronate, pamidronate or residronate) promote apoptosis in mouse osteoclasts in vitro and in vivo. (Hughes, et al., supra at S347). M-CSF, which has previously been found to be essential for osteoclast formation can suppress apoptosis, suggesting not only that maintenance of osteoclast populations, but also that formation of these multinucleated cells may be determined by apoptosis events. (Fuller, et al., *J. Bone Min. Res.* 8, S384 (1993); Perkins, et al., *J. Bone Min. Res.* 8, S390 (1993)). Local injections of IL-1 over the calvaria of mice once daily for 3 days induces intense and aggressive remodeling. (Wright, et al., *J. Bone Min. Res.* 9, S174 (1994)). In these studies. 1% of osteoclasts were apoptotic 1 day after treatment, which increased 3 days later to 10%. A high percentage (95%) of these apoptotic osteoclasts were at the reversal site. This data suggests that Caspases are functionally very important in osteoclast apoptosis.

Therefore, one aspect of the present invention is the promotion of apoptosis in osteoclasts as a novel therapy for inhibiting resorption in diseases of excessive bone loss, such as osteoporosis, using compounds of Formula (I) as defined herein.

Apoptosis can been induced by low serum in highly differentiated rat osteoblast-like (Ros 17/2.8) cells (Ihbe, et al., (1994) *J. Bone Min. Res.* 9, S167)). This was associated with a temporal loss of osteoblast phenotype, suggesting that maintenance of lineage specific gene expression and apoptosis are physiologically linked. Fetal rat calvaria derived osteoblasts grown in vitro undergo apoptosis and this is localized to areas of nodule formation as indicated by in situ end-labeling of fragmented DNA. (Lynch, et al., (1994) *J. Bone Min. Res.* 9, S352). It has been shown that the immediate early genes c-fos and c-jun are expressed prior to apoptosis; c-fos and c-jun-Lac Z transgenic mice show constitutive expression of these transcription factors in very few tissues, one of which is bone (Smeyne, et al., (1992) *Neuron.* 8, 13–23; and Morgan, J. (1993) Apoptotic Cell Death: Functions and Mechanisms. Cold Spring Harbor 13–15th October). Apoptosis was observed in these animals in the epiphyseal growth plate and chondrogenic zones as the petula ligament calcifies. Chondrogenic apoptosis has also been observed in PTHRP-less mice and these transgenics exhibit abnormal endochondral bone formation (Lee, et al., (1994) *J. Bone Min. Res.* 9, S159). A very recent paper examined a human osteosarcoma cell line which undergoes spontaneous apoptosis. Using this cell line, LAP-4, but not ICE, could be detected and in vitro apoptosis could be blocked by inhibition or depletion of LAP-4 (Nicholson, et al., (1995) *Nature* 376, 36–43). Thus, apoptosis may play a role in loss of osteoblasts and chondrocytes and inhibition of apoptosis could provide a mechanism to enhance bone formation.

Therefore, another aspect of the present invention is the inhibition of apoptosis as a novel therapy to enhance bone formation using compounds of Formula (I) as defined herein.

Osteoarthritits (OA) is a degenerative disease characterized by progressive erosion of articular cartilage. Chondrocytes are the single cell-type found in articular cartilage and perturbations in metabolism of these cells may be involved in the pathogenesis of OA. Injury to cartilage initiates a specific reparative response which involves an increase in the production of proteoglycan and collagen in an attempt to reestablish normal matrix homeostasis. However, with the progress of the disease, the 3-dimensional collagen network is disrupted and cell death of chondrocytes occurs in OA lesions (Malemud, et al.: Regulation of chondrocytes in osteoarthritis. In: Adolphe, M. ed. Biological Regulation of Chondrocytes, Boca Raton: CRC Press, 1992, 295–319). It has been shown that in OA, chondrocytes adjacent to cartilage defects express high levels of bcl-2 (Erlacher, et al., (1995) *J. of Rheumatology,* 926–931). This represents an attempt to protect chondrocytes from apoptosis induced by the disease process.

Protection of chondrocytes during early degenerative changes in cartilage by inhibition of apoptosis may provide a novel therapeutic approach to this common disease. Therefore, another aspect of the present invention is the inhibition of apoptosis as a novel therapy to treat osteoarthritis, using compounds of Formula (I) as defined herein.

Recent evidence shows that chronic, degenerative conditions of the liver are linked to hepatocellular apoptosis. These conditions include chemical-, infectious- and immune/inflammatory-induced heptocellular degeneration. Apoptosis of liver cells has been observed in liver degenerative states induced by a variety of chemical agents, including acetaminophen (Ray, et al., (1993) *FASEB. J.* 7, 453–463), cocaine (Cascales, et al., (1994) *Hepatology* 20, 992–1001) and ethanol (Baroni, etal., (1994) *J. Hepatol.* 20, 508–513). Infectious agents and their chemical components that have been shown to induce apoptosis include hepatitis ((Hiramatsu, et al., (1994) *Hepatology* 19, 1354–1359; Mita, et al., (1994) *Biochem. Biophys. Res. Commun.* 204, 468–474)), tumor necrosis factor and endotoxin. (Leist, et al., (1995) *J. Immunol.* 154, 1307–1316; and Decker, K. (1993) *Gastroenterology* 28(S4), 20–25). Stimulation of immune/inflammatory responses by mechanisms such as allograft transplantation and hypoxia followed by reperfusion have been shown to induce apoptosis of hepatocytes (Drams, et al., (1995) *Transplant. Proc.* 27, 466–467). Together, this evidence supports that hepatocellular apoptosis is central to degenerative liver diseases.

Therefore, another aspect of the present invention is the inhibition of apoptosis as a novel therapy to treat degenerative liver diseases, using compounds of Formula (I) as defined herein.

Apoptosis is recognized as a fundamental process within the immune system where cell death shapes the immune system and effects immune functions. Apoptosis also is implicated in viral diseases (e.g AIDS). Recent reports indicate that HIV infection may produce an excess of apoptosis, contributing to the loss of $CD4^+$ T cells. Of additional interest is the observation that APO-1/Fas shares sequences homology with HIV-1 gp120.

Therefore, another aspect of the present invention is the inhibition of apoptosis as a novel therapy to treat viral diseases, using compounds of Formula (I) as defined herein.

Additional therapeutic directions and other indications in which inhibition of apoptotic cysteine proteases is of therapeutic utility, along with relevant citations in support of the involvement for apoptosis in each indication, are presented below in Table 1.

TABLE 1

Therapeutic Indications Related To Apoptosis

| Indication | Citations |
| --- | --- |
| Ischemia/reperfusion | Barr et al., (1994) BioTechnology 12, 487–493: Thompson, C. B. (1995) Science 267, 1456–1462 |
| Stroke | Barr et al supra; and Thompson, C., supra |
| Polycystic kidney disease | Barr et al., supra; and Mondain, et al., (1995) ORL J. Otorhinolaryngol. Relat. Spec. 57. 28–32 |
| Glomerulo-nephritis | Barr et al., supra |
| Osteoporosis | Lynch et al., (1994) J. Bone Min. Res. 9, S352; Nicholson et al., (1995) Nature 376, 37–43 |
| Erythropoiesis/ Aplastic anemia | Thompson. C., supra; Koury et al., (1990) Science 248. 378–381 |
| Chronic liver degeneration | Thompson, C., supra; Mountz et al., (1994) Arthritis Rheum. 37 1415–1420; Goldin et al., (1993) Am. J. Pathol. 171, 73–76 |
| T-cell death | Thompson, C., supra; Ameison et al., (1995) Trends Cell Biol. 5, 27–32 |
| Osteoarthritis - chondrocytes | Ishizaki et al., (1994) J. Cell Biol. 126, 1069–1077; Blanco et al., (1995) Am. J. Pathol. 146, 75–85 |
| Male pattern baldness | Mondain et al., supra; Seiberg et al., (1995) J. Invest. Dermatol. 104, 78–82; Tamada et al., (1994) Br. J. Dermatol. 131, 521–524 |
| Alzheimer's disease | Savill, J., (1994) Eur. J. Clin. Invest. 24, 715–723; Su et al., (1994) Neuroreport 5, 2529–2533; Johnson, E., (1994) Neurorepory 5, Aging 15 Suppl. 2, S187–S189 |
| Parkinson's disease | Savil, J., supra; Thompson, C., supra |
| Type I diabetes | Barr et al., supra |

The IL-1 and TNF inhibiting effects of compounds of the present invention are determined by the following in vitro assays:

Interleukin—1 (IL-1)

Human peripheral blood monocytes are isolated and purified from either fresh blood preparations from volunteer donors, or from blood bank buffy coats, according to the procedure of Colotta et al, J Immunol, 132, 936 (1984). These monocytes ($1 \times 10^6$) are plated in 24-well plates at a concentration of 1–2 million/ml per well. The cells are allowed to adhere for 2 hours, after which time non-adherent cells are removed by gentle washing. Test compounds are then added to the cells for about 1 hour before the addition of lipopolysaccharide (50 ng/ml), and the cultures are incubated at 37° C. for an additional 24 hours. At the end of this period, culture super-natants are removed and clarified of cells and all debris. Culture supernatants are then immediately assayed for IL-1 biological activity, either by the method of Simon et al., J. Immunol. Methods, 84, 85. (1985) (based on ability of IL-1 to stimulate a Interleukin 2 producing cell line (EL-4) to secrete IL-2, in concert with A23187 ionophore) or the method of Lee et al., J. Immuno Therapy, 6 (1), 1–12 (1990) (ELISA assay).

Tumour Necrosis Factor (TNF):

Human peripheral blood monocytes are isolated and purified from either blood bank buffy coats or platelet pheresis residues, according to the procedure of Colotta, R. et al., J Immunol. 132(2), 936 (1984). The monocytes are plated at a density of $1 \times 10^6$ cells/ml medium/well in 24-well multidishes. The cells are allowed to adhere for 1 hour after which time the supernatant is aspirated and fresh medium (1 ml, RPMI-1640, Whitaker Biomedical Products, Whitaker, Calif.) containing 1% fetal calf serum plus penicillin and streptomycin (10 units/ml) added. The cells are incubated for 45 minutes in the presence or absence of a test compound at 1 nM–10 mM dose ranges (compounds are solubilized in dimethyl sulfoxide/ethanol, such that the final solvent concentration in the culture medium is 0.5% dimethyl sulfoxide/0.5% ethanol). Bacterial lipopoly-saccharide (*E. coli* 055:B5 [LPS] from Sigma Chemicals Co.) is then added (100 ng/ml in 10 ml phosphate buffered saline) and cultures incubated for 16–18 hours at 37° C. in a 5% $CO_2$ incubator. At the end of the incubation period, culture supernatants are removed from the cells, centrifuged at 3000 rpm to remove cell debris. The supernatant is then assayed for TNF activity using either a radio-immuno or an ELISA assay, as described in WO 92/10190 and by Becker et al., J Immunol, 1991, 147, 4307.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of formula

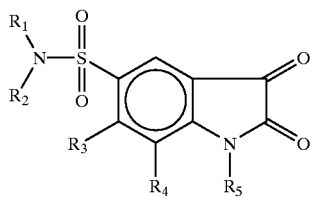

wherein
$R_1$ is hydrogen, or $C_{1-4}$ alkyl;
$R_2$ is $C_{1-10}$ alkyl, substituted or unsubstituted aryl $C_{1-4}$ alkyl, substituted or unsubstituted heteroaryl $C_{1-4}$ alkyl, substituted or unsubstituted $C_{3-7}$ cycloalkyl, or $R_1$ and $R_2$ together with the nitrogen to which they are attached form a 3 to 10 membered ring which contains or does not contain an additional heteroatom selected from oxygen, nitrogen or sulfur;
$R_3$ and $R_4$ are $C_{1-6}$ alkyl, hydrogen, nitro or halogen and
$R_5$ is $C_{1-6}$ alkyl, hydrogen, arylalkyl or heteroarylalkyl.

2. A compound according to claim 1 wherein $R_5$ is substituted benzyl.

3. A compound according to claim 1 wherein $R_1$ is hydrogen or methyl.

4. A compound wherein $R_1$ and $R_2$ are joined to form a five membered nitrogen containing ring.

5. The compound according to claim 1 which is
(S)-(+)-5-[1-(2-Methoxymethylpyrrolidinyl)sulfonyl]isatin,
DL-5-[1-(2-(Hydroxyethyl)piperidinyl)sulfonyl]isatin,
(+/−)-5-[1-(3-Hydroxymethyl)piperidinyl)sulfonyl]isatin,
(S)-(+)-5-[1-(2-Hydroxymethylpyrrolidinyl)sulfonyl]isatin,
(S)-(+)-5-[1-(2-Benzyloxycarbonylpyrrolidinyl)sulfonyl]isatin,
5-[N-(N-Methyl-2-hydroxyethylamino)sulfonyl]isatin,
5-[N-(N-Methyl-2-(4-pyridine)ethylamino)sulfonyl]isatin,
5-[N-(N'-Benzylpiperazine)sulfonyl]isatin,
(R)-(−)-5-[1-(2-Methoxymethylpyrrolidinyl)sulfonyl]isatin,
(S)-(+)-5-[1-(2-Methoxycarbonylpyrrolidinyl)sulfonyl]isatin,
5-[N-(N-Methylanilino)sulfonyl]isatin,
(S)-(+)-5-[1-(2-t-Butoxycarbonylpyrrolidinyl)sulfonyl]isatin,
(S)-(+)-5-[1-(2-N,N-Dimethylaminocarbonylpyrrolidinyl)sulfonyl]isatin,
(S)-(+)-5-[1-(2-Carboxypyrrolidinyl)sulfonyl]isatin,
(S)-(+)-1-Isopropyl-5-[1-(2-Methoxymethylpyrrolidinyl)sulfonyl]isatin,
5-[N-(N-Methyl-2-cyanoethylamino)sulfonyl]isatin,
(S)-(+)-5-[1-(2-(Anilinomethyl)pyrrolidinyl)sulfonyl]isatin,
5-[N-(Ethoxycarbonylmethylamino)sulfonyl]isatin,
(+/−)-5-[1-(3-(N-Methyl-N-Boc-amino)pyrrolidinyl)sulfonyl]isatin,
(+/−)-5-[1-(3-(N-Methyl-N-phenethylcarbonylamino)pyrrolidinyl)sulfonyl]isatin,
(+/−)-5-[1-(3-(N-Methylamino)pyrrolidinyl)sulfonyl]isatin trifluoro acetic acid salt,
5-[N-(N-methyl-2-Methoxyethylamino)sulfonyl]isatin,
(S)-(+)-5-[1-(2-Phenoxymethylpyrrolidinyl)sulfonyl]isatin,
(S)-(+)-5-[1-(2-Thiophenoxymethylpyrrolidinyl)sulfonyl]isatin,
(S)-(+)-5-[1-(2-Phenylaminocarbonylpyrrolidinyl)sulfonyl]isatin,
(+/−)-5-[1-(3-Chloromethylpiperidinyl)sulfonyl]isatin,
5-[1-(4-Hydroxypiperidinyl)sulfonyl]isatin,
5-[N-(Morpholino)sulfonyl]isatin,
5-[N-(N-Methyl-2-phenethylamino)sulfonyl]isatin,
(S)-(+)-1-Benzyl-5-[1-(2-thiophenoxymethylpyrrolidinyl)sulfonyl]isatin,
(+/−)-5-[1-(3-(N-methylbenzamide)pyrrolidinyl)sulfonyl]isatin,
5-[1-(2-(Phenylsulfinylmethyl)pyrrolidinyl)sulfonyl]isatin,
5-[1-(azetidinyl)sulfonyl]isatin,
(S)-(+)-5-[1-(2-(4-Methylphenoxymethyl)pyrrolidinyl)sulfonyl]isatin,
(S)-(+)-5-[1-(2-(4-Methoxyphenoxymethyl)pyrrolidinyl)sulfonyl]isatin,
(S)-(+)-5-[1-(2-(4-Chlorophenoxymethyl)pyrrolidinyl)sulfonyl]isatin,
(S)-(+)-5-[1-(2-(3,4-Dichlorophenoxymethyl)pyrrolidinyl)sulfonyl]isatin,
5-[1-(2-(4-chlorophenoxy)azetidinyl)sulfonyl]isatin,
5-[1-(Homopiperidinyl)sulfonyl]isatin,
(S)-(+)-1-(3-Chlorobenzyl)-5-[1-(2-phenoxymethylpyrrolidinyl)sulfonyl]isatin,
(S)-(+)-1-Benzyl-5-[1-(2-phenoxymethylpyrrolidinyl)sulfonyl]isatin,
5-[1-(Pyrrolidinyl)sulfonyl]isatin,
(S)-(+)-1-(4-Methylbenzyl)-5-[1-(2-phenoxymethylpyrrolidinyl)sulfonyl]isatin,
(S)-(+)-1-(4-Chlorobenzyl)-5-[1-(2-phenoxymethylpyrrolidinyl)sulfonyl]isatin,
(S)-(+)-1-(3,4-Dichlorobenzyl)-5-[1-(2-phenoxymethylpyrrolidinyl)sulfonyl]isatin,
(S)-(+)-1-(2-Methylnapthalene)-5-[1-(2-phenoxymethylpyrrolidinyl)sulfonyl]isatin,
(S)-(+)-1-[4-(1,2,3-Thiadiazole)benzyl]-5-[1-(2-phenoxymethylpyrrolidinyl)sulfonyl]isatin,
(S)-(+)-1-Allyl-5-[1-(2-phenoxymethylpyrrolidinyl)sulfonyl]isatin,
(S)-(+)-1-(2-Phenylethyl)-5-[1-(2-phenoxymethylpyrrolidinyl)sulfonyl]isatin,
(S)-(+)-1-(3-Phenylpropyl)-5-[1-(2-phenoxymethylpyrrolidinyl)sulfonyl]isatin,
(S)-(+)-1-(4-Methoxybenzyl)-5-[1-(2-phenoxymethylpyrrolidinyl)sulfonyl]isatin,
(S)-(+)-1-Cyclohexylmethyl-5-[1-(2-phenoxymethylpyrrolidinyl)sulfonyl]isatin, (S)-(+)-1-Methyl-5-[1-(2-phenoxymethylpyrrolidinyl) sulfonyl]isatin,
(S)-(+)-1-(3-Iodobenzyl)-5-[1-(2-phenoxymethylpyrrolidinyl)sulfonyl]isatin,
(S)-(+)-1-Methyl-5-[1-(2-N-methylanilinomethyl) pyrrolidinyl)sulfonyl]isatin,
(S)-(+)-1-(t-Butoxycarbonylmethyl)-5-[1-(2-phenoxymethylpyrrolidinyl)sulfonyl]isatin,
(S)-(+)-1-(Acetic acid)-5-[1-(2-phenoxymethylpyrrolidinyl) sulfonyl]isatin,
(S)-(+)-1-Methyl-5-[1-(2-(anilinomethyl)pyrrolidinyl) sulfonyl]isatin,
(R)-(−)-5-[1-(2-(anilinomethyl)pyrrolidinyl)sulfonyl]isatin,
(S)-(+)-1-Benzyl-5-[1-(2-(anilinomethyl)pyrrolidinyl) sulfonyl]isatin,
(S)-(+)-1-Cyanomethyl-5-[1-(2-phenoxymethylpyrrolidinyl)sulfonyl]isatin,
(S)-(+)-1-[2-(2-Ethyl)-1-methylpyrrolidine]-5-[1-(2-phenoxymethylpyrrolidinyl)sulfonyl]isatin,
(S)-(+)-1-(3-Methylsulfonylbenzyl)-5-[1-(2-phenoxymethylpyrrolidinyl)sulfonyl]isatin,
(S)-(+)-1-(3-Carboxamidobenzyl)-5-[1-(2-phenoxymethylpyrrolidinyl)sulfonyl]isatin,
(R)-5-[1-(2-Phenethylpyrrolidinyl)sulfonyl]isatin,
5-[1-(2-Phenoxymethylpiperdinyl)sulfonyl]isatin,
(S)-5-[1-(1-Methoxy-2-phenethylpyrrolidinyl)sulfonyl] isatin,
(S)-1-(4-Pyridinylmethyl)-5-[1-(2-phenoxymethylpyrrolidinyl)sulfonyl]isatin,
(S)-1-(3-Pyridinylmethyl)-5-[1-(2-phenoxymethylpyrrolidinyl)sulfonyl]isatin,
5-[1-(N-Acetylhomopiperazine)sulfonyl]isatin,
5-[1-(Thiazolidine)sulfonyl]isatin,
5-[1-(4-Piperanoylpiperazine)sulfonyl]isatin,
(S)-1-[3-(t-Butoxycarbonyl)benzyl]-5-[1-(2-phenoxymethylpyrrolidinyl)sulfonyl]isatin,
(S)-1-(3-Carboxyphenylmethyl)-5-[1-(2-phenoxymethylpyrrolidinyl)sulfonyl]isatin,
5-[1-(4-Acetyl-(2-thiophene)-homopiperazine)sulfonyl] isatin,
(S)-1-(4-Cyanophenylmethyl)-5-[1-(2-phenoxymethylpyrrolidinyl)sulfonyl]isatin,
(S)-1-(3,4-Methylenedioxybenzyl)-5-[1-(2-phenoxymethylpyrrolidinyl)sulfonyl]isatin,
(S)-1-(Methoxymethyl)-5-[1-(2-phenoxymethylpyrrolidinyl)sulfonyl]isatin,
(S)-1-[3-(t-Butoxycarbonyl)propyl]-5-[1-(2-phenoxymethylpyrrolidinyl)sulfonyl]isatin,
(S)-1-(3-Carboxypropyl)-5-[1-(2-phenoxymethylpyrrolidinyl)sulfonyl]isatin,
(S)-1-[4-(t-Butoxycarbonyl)phenylmethyl]-5-[1-(2-phenoxymethylpyrrolidinyl)sulfonyl]isatin, or
(S)-1-(4-Carboxyphenylmethyl)-5-[1-(2-phenoxymethylpyrrolidinyl)sulfonyl]isatin.

6. A pharmaceutical composition comprising a compound according to claim 1 and a pharmaceutically acceptable carrier or diluent.

7. A method of blocking excess or inappropriate apoptosis in a mammal in need of such treatment which method comprises administering to said mammal or human an effective amount of a compound of Formula (I) according to claim 1, or a pharmaceutically acceptable salt thereof.

8. The method according to claim 7 wherein the excessive or inappropriate apoptosis occurs in Alzeheimer disease.

9. The method according to claim 7 wherein the excessive or inappropriate apoptosis occurs in viral infections.

10. The method according to claim 7 wherein the excessive or inappropriate apoptosis occurs during infarction or reperfusion injury.

11. The method according to claim 7 wherein the excessive or inappropriate apoptosis occurs during ischemia.

12. The method according to claim 7 wherein the excessive or inappropriate apoptosis results in excessive bone loss.

13. The method according to claim 7 wherein the excessive or inappropriate apoptosis results in the disease of osteoarthritis.

14. The method according to claim 7 wherein the excessive or inappropriate apoptosis results in hepatocellular degeneration.

15. A method for the treatment of diseases or disorders associated with excessive IL-1β convertase activity, in a mammal in need thereof, which method comprises administering to said mammal an effective amount of a compound of Formula (I) according to claim 1, or a pharmaceutically acceptable salt thereof.

16. A method of blocking, inhibiting, or decreasing the production of IL-1β and/or TNF, in a mammal in need of such treatment, which method comprises administering to said mammal an effective amount of a compound of Formula (I) according to claim 1, or a pharmaceutically acceptable salt thereof.

17. A method for inhibiting the production of caspase 3 and 7 in a mammal in need of such treatment, which method comprises administering to said mammal an effective amount of a compound of Formula I according to claim 1, or a pharmaceutically acceptable salt thereof.

* * * * *